(12) United States Patent
Nematihosseinabadi et al.

(10) Patent No.: US 11,948,690 B2
(45) Date of Patent: Apr. 2, 2024

(54) PULMONARY FUNCTION ESTIMATION

(71) Applicant: SAMSUNG ELECTRONICS CO., LTD., Gyeonggi-Do (KR)

(72) Inventors: Ebrahim Nematihosseinabadi, Mountain View, CA (US); Md M. Rahman, San Jose, CA (US); Viswam Nathan, Sunnyvale, CA (US); Korosh Vatanparvar, Santa Clara, CA (US); Jilong Kuang, San Jose, CA (US); Jun Gao, Menlo Park, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 518 days.

(21) Appl. No.: 16/716,206

(22) Filed: Dec. 16, 2019

(65) Prior Publication Data
US 2021/0027893 A1 Jan. 28, 2021

Related U.S. Application Data

(60) Provisional application No. 62/877,677, filed on Jul. 23, 2019.

(51) Int. Cl.
*G16H 50/30* (2018.01)
*G06N 20/00* (2019.01)
*G10L 25/24* (2013.01)
*G10L 25/66* (2013.01)
(Continued)

(52) U.S. Cl.
CPC ............. *G16H 50/30* (2018.01); *G06N 20/00* (2019.01); *G10L 25/24* (2013.01); *G10L 25/66* (2013.01); *G16H 10/60* (2018.01); *G16H 20/30* (2018.01)

(58) Field of Classification Search
None
See application file for complete search history.

(56) References Cited

U.S. PATENT DOCUMENTS

| 6,168,568 B1 | 1/2001 | Gavriely |
| 10,028,675 B2 | 7/2018 | Patel et al. |
| 10,199,042 B2 | 2/2019 | Rodriguez et al. |

(Continued)

FOREIGN PATENT DOCUMENTS

| JP | 2001505085 A | 4/2001 |
| JP | 2007029258 A | 2/2007 |

(Continued)

OTHER PUBLICATIONS

B. H. Tracey et al., Cough detection algorithm for monitoring patient recovery from pulmonary tuberculosis, 2011 Annual International Conference of the IEEE Engineering in Medicine and Biology Society 6017-6020 (2011), https://ieeexplore.ieee.org/abstract/document/6091487 (last visited May 20, 2022) (Year: 2011).*

(Continued)

*Primary Examiner* — Jonathon A. Szumny
*Assistant Examiner* — Nicholas Akogyeram, II
(74) *Attorney, Agent, or Firm* — Cuenot, Forsythe & Kim, LLC

(57) ABSTRACT

Pulmonary function estimation can include detecting one or more cough events from a time series of audio signals generated by an electronic device of a user. Based on the one or more cough events, one or more lung function metrics of the user can be determined.

18 Claims, 13 Drawing Sheets

(51) Int. Cl.
*G16H 10/60* (2018.01)
*G16H 20/30* (2018.01)

(56) References Cited

U.S. PATENT DOCUMENTS

| | | | |
|---|---|---|---|
| 10,258,753 B2 | 4/2019 | Adams et al. | |
| 10,285,624 B2 | 5/2019 | Taylor et al. | |
| 10,391,270 B2 | 8/2019 | Adams et al. | |
| 2003/0013946 A1* | 1/2003 | Schau | A61B 5/087 600/300 |
| 2008/0082018 A1* | 4/2008 | Sackner | A61B 5/113 600/529 |
| 2008/0275349 A1* | 11/2008 | Halperin | A61B 5/447 600/364 |
| 2009/0171231 A1* | 7/2009 | Caro | A61B 8/08 600/529 |
| 2010/0234758 A1 | 9/2010 | De Menezes | |
| 2012/0277583 A1* | 11/2012 | Addington | A61B 5/08 600/431 |
| 2013/0149388 A1* | 6/2013 | McClay | G01N 24/08 73/61.41 |
| 2013/0237863 A1* | 9/2013 | Song | A61B 5/113 600/529 |
| 2014/0336537 A1* | 11/2014 | Patel | A61B 7/003 600/586 |
| 2015/0073306 A1* | 3/2015 | Abeyratne | A61B 5/742 600/586 |
| 2015/0126888 A1* | 5/2015 | Patel | G16H 50/30 600/538 |
| 2017/0071506 A1* | 3/2017 | Dwarika | H04W 4/50 |
| 2017/0127977 A1* | 5/2017 | Weffers-Albu | A61B 5/113 |
| 2017/0325779 A1* | 11/2017 | Spina | A61B 5/0205 |
| 2018/0035901 A1* | 2/2018 | Cronin | A61B 5/00 |
| 2018/0129786 A1* | 5/2018 | Khine | G16H 40/63 |
| 2018/0177432 A1* | 6/2018 | Au | A61B 7/003 |
| 2019/0336039 A1* | 11/2019 | Hines | A61B 5/1107 |
| 2019/0336077 A1* | 11/2019 | Kuhn | A61B 5/14546 |
| 2020/0015709 A1* | 1/2020 | Peltonen | A61B 5/7203 |
| 2020/0312321 A1* | 10/2020 | Voix | G06F 18/217 |

FOREIGN PATENT DOCUMENTS

| | | | |
|---|---|---|---|
| JP | 2018028882 A | 2/2018 | |
| WO | 2006129098 A2 | 12/2006 | |
| WO | WO-2016091612 A1 * | 6/2016 | A61B 5/0205 |
| WO | 2019119050 A1 | 6/2019 | |

OTHER PUBLICATIONS

Thomas V Herregods et al., Determinants of reflux-induced chronic cough, 66 GUT 2057-2062 (2017), https://gut.bmj.com/content/gutjnl/66/Dec.2057.full.pdf (last visited May 20, 2022), hereinafter referred to as Herregods (Year: 2017).*

Miguel Fernandez-Granero, Daniel Sanchez-Morillo & Antonio Leon-Jimenez, Computerised analysis of telemonitored respiratory sounds for predicting acute exacerbations of COPD, 15 Sensors 26978-26996 (2015), https://www.mdpi.com/1424-8220/15/10/26978 (last visited Nov. 16, 2023) (Year: 2015).*

WIPO Application PCT/KR2020/002180, Int'l. Search Report and Written Opinion, dated May 29, 2020, 10 pg.

Nemati, E. et al., "Private audio-based cough sensing for in-home pulmonary assessment using mobile devices," In Proc. of the 13th EAI International Conference on Body Area Networks, Oct. 2018, 12 pg.

Larson, E.C. et al., "SpiroSmart: using a microphone to measure lung function on a mobile phone," In Proc. of the 2012 ACM Conf. on Ubiquitous Computing, Sep. 5, 2012, pp. 280-289, ACM.

Goel, M. et al., "Spirocall: Measuring lung function over a phone call," In Proc. of the 2016 CHI Conference on Human Factors in Computing Systems, May 7, 2016, pp. 5675-5685, ACM.

* cited by examiner

1000

```
┌─────────────────────────────────────────────────────────┐
│ Detect one or more cough events from a time-based series of audio │
│   signals generated by an electronic device of a user.  │
│                          1002                           │
└─────────────────────────────────────────────────────────┘
                              │
                              ▼
┌─────────────────────────────────────────────────────────┐
│ Determine one or more lung function metrics of the user based on │
│              the one or more cough events.              │
│                          1004                           │
└─────────────────────────────────────────────────────────┘
```

```
┌─────────────────────────────────────────────────────┐
│ Detect one or more cough events from a time-based   │
│ series of audio signals generated by an electronic  │
│ device of a user.                                   │
│                      1102                            │
└─────────────────────────────────────────────────────┘
                          │
                          ▼
┌─────────────────────────────────────────────────────┐
│ Generate a plurality of features relevant to cough  │
│ Characteristics associated with the one or more     │
│ cough events.                                       │
│                      1104                            │
└─────────────────────────────────────────────────────┘
                          │
                          ▼
┌─────────────────────────────────────────────────────┐
│ Select one or more features from the plurality of   │
│ features based on contextual information relating   │
│ to the user.                                        │
│                      1106                            │
└─────────────────────────────────────────────────────┘
                          │
                          ▼
┌─────────────────────────────────────────────────────┐
│ Determine lung function metric(s) based on the one  │
│ or more features selected from the plurality of     │
│ features.                                           │
│                      1108                            │
└─────────────────────────────────────────────────────┘
```

┌─────────────────────────────────────────────────────────────┐
│ Segment one or more cough events into a plurality of segments. │
│                            1202                             │
└─────────────────────────────────────────────────────────────┘
                              ↓
┌─────────────────────────────────────────────────────────────┐
│ Determine a cough burst segment from the plurality of segments. │
│                            1204                             │
└─────────────────────────────────────────────────────────────┘
                              ↓
┌─────────────────────────────────────────────────────────────┐
│  Select one or more features from a plurality of features based on │
│                    the cough burst segment.                 │
│                            1206                             │
└─────────────────────────────────────────────────────────────┘
                              ↓
┌─────────────────────────────────────────────────────────────┐
│ Determine one or more lung function metrics of the user based │
│            on the one or more features selected.            │
│                            1208                             │
└─────────────────────────────────────────────────────────────┘

FIG. 12

PULMONARY FUNCTION ESTIMATION

CROSS-REFERENCE TO RELATED APPLICATIONS

This application claims the benefit of U.S. Provisional Patent Application No. 62/877,677 filed on Jul. 23, 2019, which is fully incorporated herein by reference.

TECHNICAL FIELD

This disclosure relates to pulmonary function testing and estimation.

BACKGROUND

Pulmonary function testing plays a dual role in both diagnosing and treating pulmonary conditions such as asthma, pulmonary fibrosis, cystic fibrosis, and chronic obstructive pulmonary disease (COPD). Spirometry is currently the most widely used diagnosis tool for assessment of the pulmonary function. Spirometry testing measures a patient's lung function by determining the volume and/or rate of the flow of the air that a patient can forcefully exhale. Among the parameters measured by a spirometer are vital capacity (VC), forced vital capacity (FVC), and forced expiratory volume (FEV) at intervals of 0.5 second, 1.0 second (FEV1), 2.0 seconds, and 3.0 seconds. Results of spirometry testing are typically given in terms of liters and liters per second, as well as percent of predicted values for patients having similar characteristics (e.g., height, weight, gender, age).

SUMMARY

In one or more embodiments, a method includes detecting, with a processor, one or more cough events from a time series of audio signals generated by an electronic device of a user. The method also includes determining, with the processor, one or more lung function metrics of the user based on the one or more cough events.

In one or more embodiments, a system includes a processor configured to initiate operations. The operations include detecting one or more cough events from a time series of audio signals generated by an electronic device of a user. The operations also include determining one or more lung function metrics of the user based on the one or more cough events.

In one or more embodiments, a computer program product includes a computer readable storage medium having instructions stored thereon. The instructions are executable by a processor to initiate operations. The operations include detecting one or more cough events from a time series of audio signals generated by an electronic device of a user. The operations also include determining one or more lung function metrics of the user based on the one or more cough events.

This Summary section is provided merely to introduce certain concepts and not to identify any key or essential features of the claimed subject matter. Other features of the inventive arrangements will be apparent from the accompanying drawings and from the following detailed description.

BRIEF DESCRIPTION OF THE DRAWINGS

The inventive arrangements are illustrated by way of example in the accompanying drawings. The drawings, however, should not be construed to be limiting of the inventive arrangements to only the particular implementations shown. Various aspects and advantages will become apparent upon review of the following detailed description and upon reference to the drawings.

FIG. 10 illustrates an example method of determining a PFT value according to an embodiment.

FIG. 11 illustrates an example method of determining a PFT value according to an embodiment.

FIG. 12 illustrates an example method of determining a PFT value according to an embodiment.

DETAILED DESCRIPTION

Figure 1:
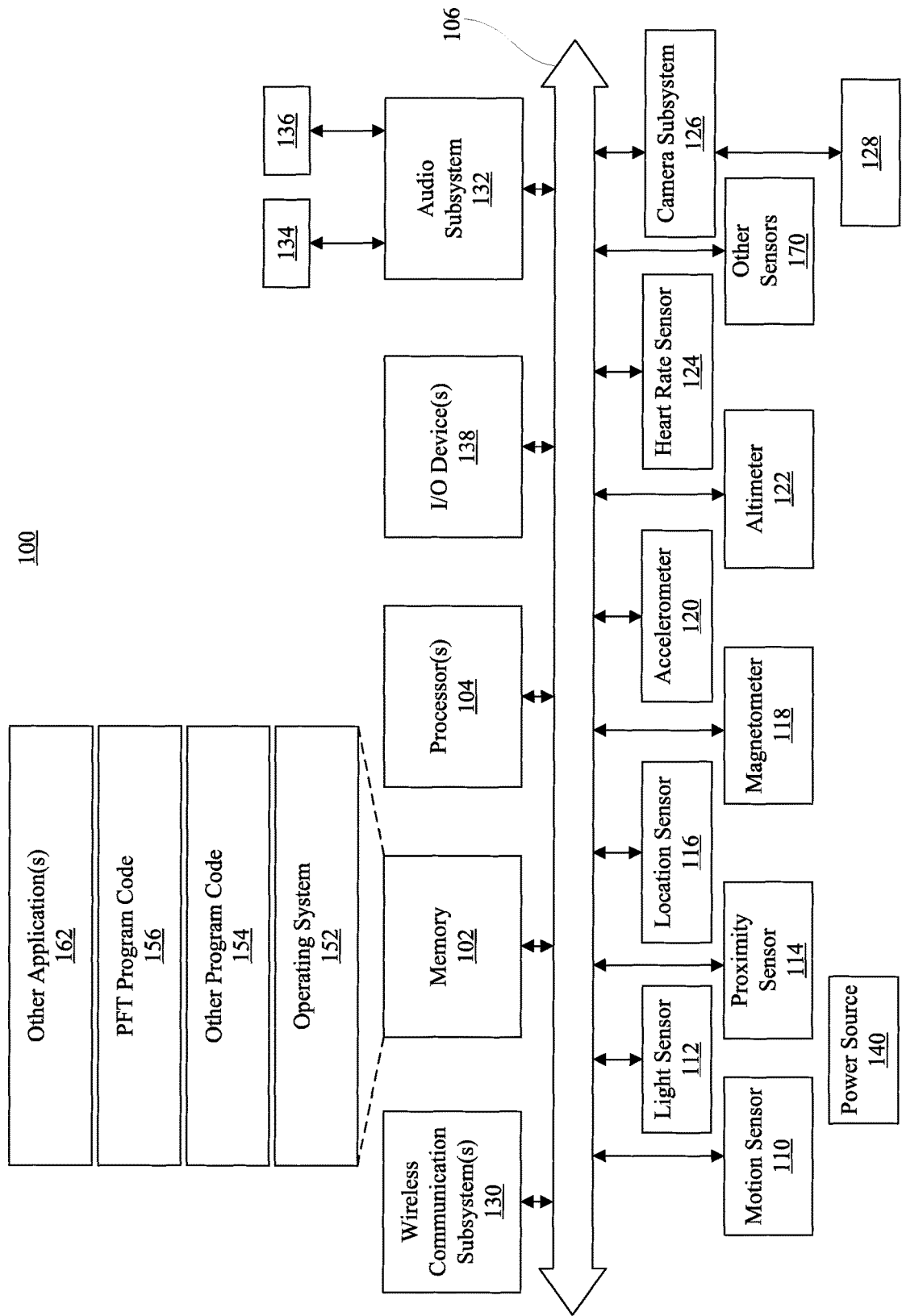
FIG. 1 illustrates an example system in accordance with one or more embodiments described herein.

While the disclosure concludes with claims defining novel features, it is believed that the various features described within this disclosure will be better understood from a consideration of the description in conjunction with the drawings. The process(es), machine(s), manufacture(s) and any variations thereof described herein are provided for purposes of illustration. Specific structural and functional details described within this disclosure are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to pulmonary function testing. Pulmonary function testing is often performed using a spirometer or similar type device. Because the reliability of the results typically depends on the way that testing is performed, pulmonary function testing is often done under the supervision of a physician or other healthcare professional in a hospital or clinic. Professionally administered testing in a hospital or clinic, however, can be costly and inconvenient for a patient. The cost and inconvenience may also lead to less frequent testing, thus making it less likely that an adverse event related to a patient's pulmonary condition can be detected early.

Self-administered testing using, for example, a portable spirometer can provide patients with a more convenient, less costly alternative. Such testing, however, presents several challenges, especially with respect to the reliability of the results obtained from self-administered testing. Patient non-compliance with standard test modalities and the lack of supervision by a healthcare professional have tended to make physicians reluctant to rely on patient-administered testing for monitoring the lung functioning of patients.

The systems and methods illustrated by the embodiments described herein address these concerns and other challenges. The inventive arrangements disclosed can be implemented, for example, in a handheld, wearable, or other mobile device, such as a smartphone or smartwatch, as well as in a home-based virtual assistant, smart TV, or similar device. The system and methods enable a user to estimate pulmonary functions with minimal effort and can assist physicians in monitoring and managing the user's pulmonary health.

Among the inventive aspects disclosed herein is the recognition of a correlation between lung function metrics and physically measurable features extracted from electronically captured audio signals generated in response to a person's cough. The correlation reflects an intrinsic similarity between (i) lung function and airway muscle movement of the person, and (ii) certain characteristics (e.g., cough force) of the person's cough. Accordingly, features relevant to cough force or other cough characteristics can be extracted from an audio signal corresponding to a cough event, and the features regressed against pulmonary function test (PFT) values obtained using a pulmonary function testing device such as a spirometer. The regression provides a stochastic function for predicting PFT values (e.g., FEC1/FVC ratio) based on features (e.g., certain mel-frequency cepstral coefficients) extracted from the audio signals generated by a person's cough. In lieu of performing spirometry testing on the individual, electronically captured audio signals (captured either in real time or from a recorded cough event) can be used to predict one or more PFT values that would otherwise have been obtained through spirometry or other type of pulmonary function testing.

Among the embodiments disclosed herein is a PFT determiner that can be implemented in a system such as a smartphone, smartwatch, virtual assistant, or other device capable of converting sounds into electrical (audio) signals and processing data extracted from the signals. The PFT determiner processes audio signals generated by a system user's cough and extracts from the audio signals physically measurable features that characterize the cough. The features extracted by the system can include, for example, a measured cough force and/or duration of the cough. The features can include mel-frequency cepstral coefficients (MFCCs) and statistical measures (e.g., mean, standard deviation, skewness, kurtosis) of audio signals modeled as random processes. As described herein, these and other physically measurable features are used by the PFT determiner to identify cough characteristics (e.g., cough force) and, based on the identified characteristics, determine one or more PFT values.

A PFT determiner, in some embodiments, determines PFT values using a regression or other prediction model trained using machine learning. PFT values (e.g., FEV1, FVC, FEV1/FVC ratio, and/or other lung function metrics) determined by the PFT determiner can be used by the PFT determiner to assess the user's breathing patterns and to identify based on the determination potential or likely user conditions such as asthma, pulmonary fibrosis, cystic fibrosis, and COPD. The PFT determiner can provide monitoring of the user's lung functioning and breathing patterns over time. For example, the PFT determiner can determine, based on the PFT values, that a user has an obstruction or restriction in the user's lung and the severity of the condition. An obstructive condition can indicate a condition such as asthma or COPD. A restrictive condition can indicate a condition such as sarcoidosis and scoliosis. The treatments for each of these diseases are different, and therefore, the PFT determiner can be used to distinguish the disease and therefore determine the treatment. Also, it can track the severity of a patient's disease and can be used to determine an appropriate treatment regimen as the severity changes. Monitoring a user's lung functioning over time with the PFT determiner can reveal a consistent degradation of the user's lung functioning based on lung function parameter measurements. The degradation revealed by the PFT determiner can indicate, for example, the need to increase the dosage of the user's inhaler or other treatment. Monitoring with a PFT determiner can detect a sudden decline in a user's FEV1, indicating that the user is possibly experiencing occupational or environmental exposures causing lung disease or intense exertion. The treatments indicated by the PFT determiner in such cases would include minimizing the user's physical activity or undertaking a location change.

Certain features among those extracted from the audio signals generated by a person's cough provide better predictors than others depending on factors specific to the user (e.g., health, gender, age). Accordingly, a PFT determiner can select among the extracted features based on user characteristics such as health condition, gender, age, and/or other biodemographic factors. In certain embodiments, a PFT determiner also analyzes data generated by sensors that monitor the user's physical condition (e.g., heart rate), level of activity, and geo-location. Based on the analysis of sensor data, the PFT determiner selects specific features among those extracted from the audio signals generated by the user's cough, the selected features being used by the PFT determiner for determining one or more PFT values.

For users suffering from an already-identified condition or disease, a PFT determiner can use cough features such as voicing parameters, skewness, kurtosis, MFCCs, burst strength of a cough, and other features to classify the user's condition or disease state. The PFT determiner can thus indicate the severity of the user's condition or disease.

Using a regression model constructed based on a sufficiently sized sample of individuals, a PFT determiner can predict a PFT value that would be obtained using a testing device such as a spirometer. The regression model provides a regression equation whose parameters are determined by regressing the values of various cough features extracted from audio signals against PFT values obtained from a sample of test subjects who are tested using a spirometer or other type of pulmonary function testing device. The PFT determiner determines one or more PFT values by extracting features from audio signals generated by the sounds of the user's cough captured by an electronic device of the user. The PFT determiner inputs the extracted features into the regression model to generate the one or more PFT values, which based on the regression, are correlated with PFT values obtained using a spirometer or other type of pulmonary function testing device.

Different regression model parameters can correspond to specific characteristics of a user, such as the user's health status, gender, age, disease stage if the user is ill, and/or other biodemographic characteristics of the user. Relatedly, certain of the features extracted by a PFT determiner from the audio signals generated in response to a cough event provide significantly better regression inputs than others depending on the biodemographic characteristics of the user.

For example, the mean value of certain MFCCs may be a better predictor variable for a user suffering from asthma, whereas skewness or standard deviation of different MFCCs may be a better predictor variable for a user afflicted with COPD. Sill other features extracted by a PFT determiner may provide better predictor variables for a healthy user or different users characterized by different biodemographic factors. Accordingly, in certain embodiments, a PFT determiner selects specific ones of the extracted features for input to the regression model based on biodemographic characteristics ("context data") specific to the user.

Thus, based on general biodemographic factors such as health status, disease stage or severity, gender, and/or age of a user, the PFT determiner selects specific ones of the features extracted from the audio input and applies the selected features to a context-specific regression model to determine one or more PFT values for the user. Other context data can include such user-specific characteristics as the user's level of physical activity or living environment (e.g., exposure to pollution). Accordingly, in some embodiments, the PFT determiner additionally generates context data by retrieving and processing sensor data related to the user. Sensor data can relate to physical activity indicated, for example, by the heart rate of the user or user movements. Exposure to certain environmental conditions can be determined based, for example, on a sensor-determined geo-location of the user. Various other factors that can affect the user's lung functions can be determined from sensor data. Based on the sensor data, the PFT determiner can select specific features extracted from audio signal input, applying the selected features to a context-specific regression model to determine one or more PFT values.

In certain embodiments, a PFT determiner segments an audio signal generated by a cough, the segmenting determined using a hybrid machine learning/rule-based signal processing algorithm. An aspect of the hybrid algorithm is envelope detection, which generates a cough envelope signal, which can be processed using a multi-level zero-crossing and slope detection module. Cough segmentation isolates and highlights specific phases of the cough, including a cough burst phase. Through signal segmentation, the PFT determiner can readily identify different phases of a cough. For example, the hybrid signal processing algorithm can identify the burst phase of a cough by extracting the edges of the burst phase from the raw audio signal. The cough burst phase closely corresponds to the forced exhalation phase of a spirometry test, thus focusing the signal analysis performed by the PFT determiner on that phase of a cough that most closely corresponds to a lung function used by a spirometer to determine a lung function metric (e.g., FEV1, FVC, FEV1/FVC ratio, or other PFT value).

A PFT determiner, in certain embodiments, automatically detects whether an active, rather than passive, measurement of the user's cough is needed. As defined herein, "active measurement" and "active monitoring" refer to measurement of a PFT metric or determination of a PFT value based on a user's voluntary coughing in response to the user being prompted to cough. By contrast, "passive measurement" and "passive monitoring" as defined herein refer to measurement of a PFT metric or determination of a PFT value based on the PFT determiner automatically detecting the user's cough (unprompted) within sounds automatically captured for the PFT determiner. In various embodiments described herein, the PFT determiner can be implemented with or integrated in a system (e.g., smartphone, smartwatch) endowed with capabilities for capturing sounds and communicating with a user via sound, text, or various other signals. The PFT determiner detects a need for active measurement of a cough by identifying any inconsistency in the PFT estimation obtained based on a passively detected cough event. The PFT determiner also can determine whether a PFT value is likely invalid for some reason and/or whether an insufficient number of coughs have been detected by the cough detector. If so, the PFT determiner can seek an active measurement by instructing the user to maintain a system (e.g., smartphone or smartwatch) in a specific position (e.g., hold the microphone of the smartphone or smartwatch at a specific angle and/or distance from the user's mouth) and to cough voluntarily for a predetermined time interval.

A PFT determiner can be used to passively and, as needed, actively collect PFT data from multiple participants who voluntarily agree to contribute data for research and/or other purposes (e.g. training PFT predictor models). The collection be passive in that zero effort is required on the part of participants. Each participant need only carry or wear a system (e.g., smartphone or smartwatch) that detects cough events from various audio signals captured by the system. If a passively obtained PFT value is inconsistent or invalid, the system can instruct a participant on the need for and how to generate an active measurement. In this way, large sets of high-quality data can be obtained by mitigating the effects of ambient noise and optimizing sound volume of cough events used to determine PFT values such as FEV1, FVC, FEV1/FVC ratio, and other lung function metrics. Active collection of data from multiple participants thus enables a more accurate estimation of the lung function in a situation where passive sensing does not provide reliable estimates of PFT determinations. An active test can also include a phone-spirometry test for calibration of the system that implements the PFT determiner as needed.

As described, a PFT determiner implemented in a hand-held or wearable device (e.g., smartphone or smartwatch), or other device (e.g., home-based virtual assistant), can estimate a user's pulmonary functions in a more natural setting (e.g., home as opposed to clinic or hospital) as the user is engaged regular daily activities.

A physician can passively monitor a patient's lung functioning using a system that implements a PFT determiner. The PFT determiner can incorporate a PFT consistency determiner that initiates active monitoring whenever passive monitoring of a cough event yields an invalid or inconsistent estimate of a lung function metric for the patient. The patient's PFT data can be uploaded over a communications network (e.g., the Internet) to a Health Insurance Portability and Accountability Act (HIPAA)-compliant server that includes a patient portal accessible to the patient and a clinician portal accessible to the patient's physician.

Further aspects of the embodiments described within this disclosure are described in greater detail with reference to the figures below. For purposes of simplicity and clarity of illustration, elements shown in the figures have not necessarily been drawn to scale. For example, the dimensions of some of the elements may be exaggerated relative to other elements for clarity. Where considered appropriate, reference numbers are repeated among the figures to indicate corresponding, analogous, or like features.

FIG. 1 illustrates an example system 100 in accordance with one or more embodiments described within this disclosure. System 100 can include a memory 102, one or more processors 104 (e.g., image processors, digital signal processors, data processors), and interface circuitry 106.

In one aspect, memory 102, processor(s) 104, and/or interface circuitry 106 are implemented as separate components. In another aspect, memory 102, processor(s) 104, and/or interface circuitry 106 are integrated in one or more integrated circuits. The various components of system 100 can be coupled, for example, by one or more communication buses or signal lines (e.g., interconnects and/or wires). In one aspect, memory 102 may be coupled to interface circuitry 106 via a memory interface (not shown).

Sensors, devices, subsystems, and/or input/output (I/O) devices can be coupled to interface circuitry 106 to facilitate the functions and/or operations described herein, including the generation of sensor data. The various sensors, devices, subsystems, and/or I/O devices may be coupled to interface circuitry 106 directly or through one or more intervening I/O controllers (not shown).

For example, motion sensor 110, light sensor 112, and proximity sensor 114 can be coupled to interface circuitry 106 to facilitate orientation, lighting, and proximity functions, respectively, of system 100. Location sensor 116 (e.g., a GPS receiver and/or processor) can be connected to interface circuitry 106 to provide geo-positioning sensor data. Electronic magnetometer 118 (e.g., an integrated circuit chip) can be connected to interface circuitry 106 to provide sensor data that can be used to determine the direction of magnetic North for purposes of directional navigation. Accelerometer 120 can be connected to interface circuitry 106 to provide sensor data that can be used to determine change of speed and direction of movement of a device in three dimensions. Altimeter 122 (e.g., an integrated circuit) can be connected to interface circuitry 106 to provide sensor data that can be used to determine altitude. Heart rate sensor 124 can be connected to interface circuitry 106 to generate sensor data and facilitate measurement of a heartbeat and the determination of a heart rate.

Camera subsystem 126 can be coupled to an optical sensor 128. Optical sensor 128 can be implemented using any of a variety of technologies. Examples of optical sensor 128 include a charged coupled device (CCD), a complementary metal-oxide semiconductor (CMOS) optical sensor, and the like. Camera subsystem 126 and optical sensor 128 can be used to facilitate camera functions, such as recording images and/or video clips (hereafter "image data"). In one aspect, image data is a subset of sensor data.

Communication functions can be facilitated through one or more wireless communication subsystems 130. Wireless communications subsystem(s) 130 can include radio frequency receivers and transmitters, optical (e.g., infrared) receivers and transmitters, and so forth. The specific design and implementation of wireless communication subsystem(s) 130 can depend on the specific type of system 100 implemented and/or the communication network(s) over which system 100 is intended to operate.

For purposes of illustration, wireless communication subsystem(s) 130 may be designed to operate over one or more mobile networks (e.g., GSM, GPRS, EDGE), a Wi-Fi network that may include a WiMax network, a short-range wireless network (e.g., a Bluetooth network), and/or any combination of the foregoing. Wireless communication subsystem(s) 130 can implement hosting protocols such that system 100 can be configured as a base station for other wireless devices.

Audio subsystem 132 can be coupled to a speaker 134 and a microphone 136 to facilitate voice-enabled functions, such as voice recognition, voice replication, digital recording, audio processing, and telephony functions. Audio subsystem 132 is able to generate audio type sensor data. In one or more embodiments, microphone 136 may be utilized as a respirator sensor.

I/O devices 138 can be coupled to interface circuitry 106. Examples of I/O devices 138 include, for example, display devices, touch-sensitive display devices, track pads, keyboards, pointing devices, communication ports (e.g., USB ports), network adapters, buttons or other physical controls, and so forth. A touch-sensitive device such as a display screen and/or a pad is configured to detect contact, movement, breaks in contact, and the like using any of a variety of touch sensitivity technologies. Example touch-sensitive technologies include, for example, capacitive, resistive, infrared, and surface acoustic wave technologies, other proximity sensor arrays or other elements for determining one or more points of contact with a touch-sensitive device, and the like. One or more of I/O devices 138 may be adapted to control functions of sensors, subsystems, and such of system 100.

System 100 further includes a power source 140. Power source 140 able to provide electrical power to various elements of system 100. In one embodiment, power source 140 is implemented as one or more batteries. The batteries may be implemented using any of a variety of different battery technologies, whether disposable (e.g., replaceable) or rechargeable. In another embodiment, power source 140 is configured to obtain electrical power from an external source and provide power (e.g., DC power) to the elements of system 100. In the case of a rechargeable battery, power source 140 further may include circuitry that is able to charge the battery or batteries when coupled to an external power source.

Memory 102 can include random access memory (e.g., volatile memory) and/or non-volatile memory, such as one or more magnetic disk storage devices, one or more optical storage devices, flash memory, and so forth. Memory 102 can store operating system 152, such as LINUX, UNIX, a mobile operating system, an embedded operating system, and the like. Operating system 152 may include instructions for handling system services and for performing hardware-dependent tasks.

Memory 102 may store additional program code 154. Examples of other program code 154 may include instructions to facilitate communicating with one or more additional devices, one or more computers, and/or one or more servers; graphic user interface processing; processing instructions to facilitate sensor-related functions; phone-related functions; electronic messaging-related functions; Web browsing-related functions; media processing-related functions; GPS and navigation-related functions; security functions; camera-related functions, including Web camera and/or Web video functions; and so forth. Memory 102 may also store one or more other applications 162.

Memory 102 may store PFT program code 156. PFT program code 156 can be adapted to implement the various embodiments of a PFT determiner as described herein. Executing on one or more processors 104, PFT program code 156 performs signal processing and other operations for predicting PFT parameters based on a series of audio signals. In one or more embodiments, PFT program code 156 facilitates the extraction of features from audio signal input to system 100 (e.g., via microphone 136 or other sound transducer). The features are relevant to one or more cough characteristics (e.g., cough force) and are input to a machine learning classification model that may be incorporated into PFT program code 156. The PFT program code 156, using the machine learning classification model, generates one or more predicted PFT values based on the extracted features. The PFT values correspond to spirometry-related lung function metrics, such as FEV1, FVC, and FEV1/FVC ratio. The PFT values can be used for the identification and determination of lung-related problems and treatment of various diseases. Further aspects of operations performed through execution of PFT program code 156 are described herein with reference to the remaining figures.

Memory 102 may also store various types of data (not shown) such as sensor data, baseline data, data obtained by way of received user input(s), and/or data obtained by way of querying one or more external data sources.

The various types of instructions and/or program code described are provided for purposes of illustration and not limitation. The program code may be implemented as separate software programs, procedures, or modules. Memory 102 can include additional instructions or fewer instructions. Moreover, various functions of system 100 may be implemented in hardware and/or software, including in one or more signal processing and/or application-specific integrated circuits.

Program code stored within memory 102 and any data used, generated, and/or operated on by system 100 are functional data structures that impart functionality to a device when employed as part of the device. Further examples of functional data structures include, for example, sensor data, data obtained via user input, data obtained via querying external data sources, baseline information, and so forth. The term "data structure" refers to a physical implementation of a data model's organization of data within a physical memory. As such, a data structure is formed of specific electrical or magnetic structural elements within a memory. A data structure imposes physical organization on the data stored in the memory that is used by a processor.

In certain embodiments, one or more of the various sensors and/or subsystems described with reference to system 100 may be separate devices that are coupled or communicatively linked to system 100 through wired or wireless connections. For example, one or more (or all) of motion sensor 110, light sensor 112, proximity sensor 114, location sensor 116, magnetometer 118, accelerometer 120, altimeter 122, heart rate sensor 124, camera subsystem 126, audio subsystem 132, and so forth may be implemented as separate systems or subsystems that operatively couple to system 100 by way of I/O devices 138 and/or wireless communication subsystem(s) 130.

One or more of the sensors may be worn directly by the user and provide data to system 100 via a wired or wireless connection. Examples of additional sensors that are not illustrated in FIG. 1, but which may be used and/or worn by a user to provide sensor data to system 100 can include, for example, electrocardiography (ECG) sensors, photoplethysmography (PPG) sensors, gyroscopes, respiratory sensors, galvanic skin response (GSR) sensors, and the like. These additional sensors are represented in FIG. 1 by "other sensors" block 170. In one or more embodiments, sensors and/or subsystems as described herein are configured to generate sensor data that is stored in a memory external to system 100. System 100 (e.g., processor(s) 104) may access externally stored sensor data for use and/or analysis as described herein.

System 100 can include fewer components than those shown or include additional components other than those shown in FIG. 1 depending on the specific type of system that is implemented. Additionally, the particular operating system and/or application(s) and/or other program code included may also vary according to system type. Moreover, one or more of the illustrative components can be incorporated into, or otherwise form a portion of, another component. For example, a processor may include at least some memory.

System 100 is provided for purposes of illustration and not limitation. A device and/or system configured to perform the operations described herein may have a different architecture than illustrated in FIG. 1. The architecture may be a simplified version of system 100 and may include a processor and memory storing instructions. The architecture may include one or more sensors as described herein. System 100, or a similar system, can collect data using the various sensors of the device or sensors coupled thereto. It should be appreciated, however, that system 100 may include fewer sensors or other additional sensors. With this disclosure, data generated by a sensor is referred to as "sensor data."

Example implementations of system 100 include, for example, a smartphone or other mobile device or phone, a wearable computing device (e.g., smartwatch), a dedicated medical device, a computer (e.g., desktop, laptop, tablet computer, virtual assistant, smart TV, other data processing system), or other suitable electronic device capable of sensing and processing the sensor data. It will be appreciated that embodiments can be deployed as a standalone device or deployed as multiple devices in a distributed client-server networked system. For example, in certain embodiments, a smartwatch can operatively couple to a mobile device (e.g., phone). The mobile device may or may not be configured to interact with a remote server and/or computer system.

Figure 2:
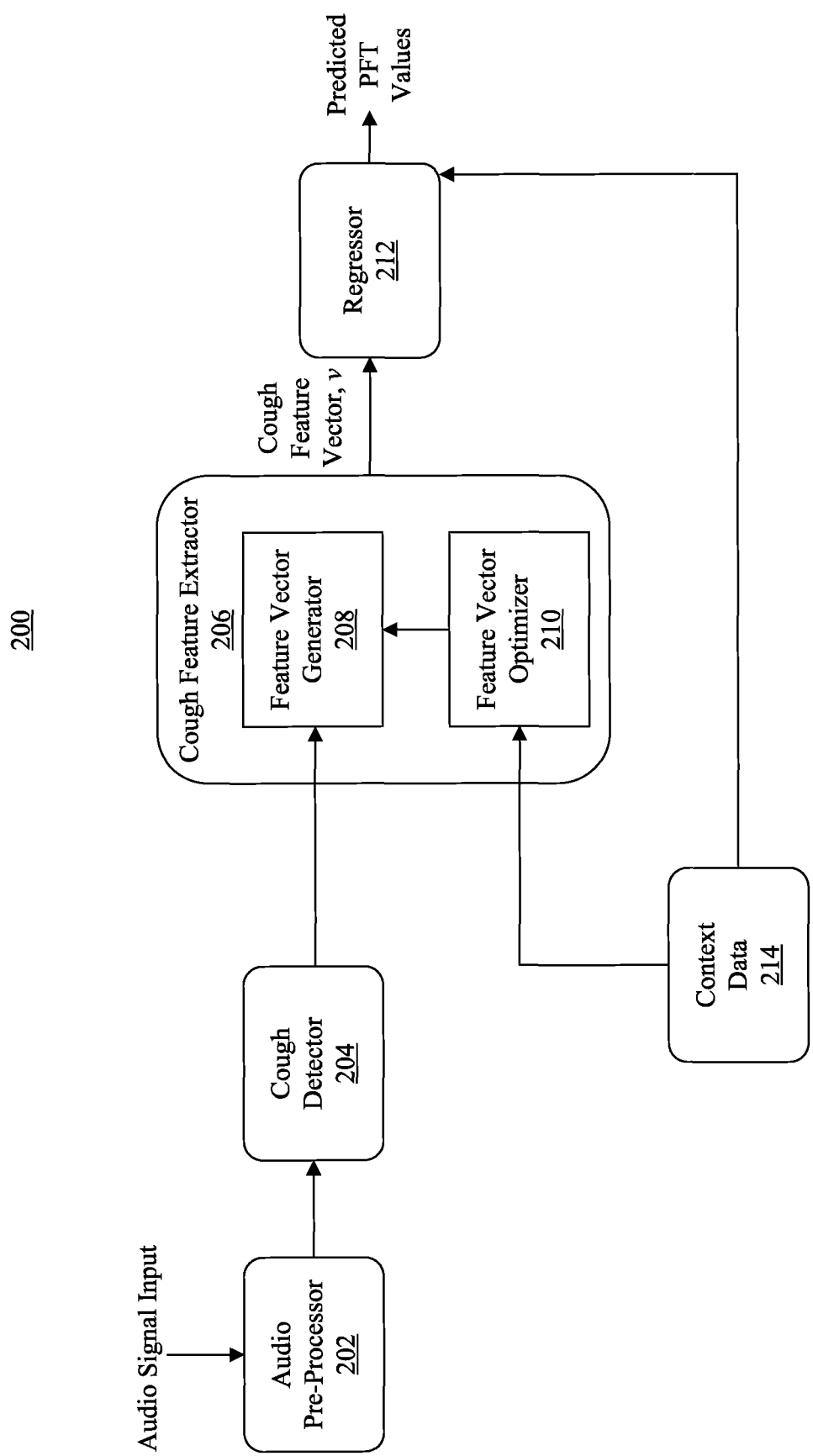
FIG. 2 illustrates an example pulmonary function test (PFT) determiner according to an embodiment.

FIG. 2 illustrates PFT determiner 200, which in one or more embodiments, detects one or more cough events from a time series of audio signals generated by an electronic device and determines one or more lung function metrics based on the one or more cough events. PFT determiner 200 illustratively includes audio pre-processor 202 operatively coupled to cough detector 204, which is operatively coupled to cough feature extractor 206. Cough feature extractor 206 illustratively comprises feature vector generator 208 and feature vector optimizer 210. Additionally, PFT determiner 200 illustratively includes regressor 212 operatively coupled to cough feature extractor 206. In one or more embodiments, PFT determiner 200 can be implemented in processor-executable instructions such as PFT program code 156 described with respect to FIG. 1. Accordingly, PFT determiner 200 can be implemented in a system such as system 100 described with respect to FIG. 1. The system can be any handheld or wearable system (e.g., smartphone or smartwatch), or stationary system (e.g., home-based virtual assistant), that includes a processor for executing program instructions and a sound transducer (microphone) for converting sounds into a series of time-varying electrical signals (audio signals). In other embodiments, PFT determiner 200 can be implemented in hardwired circuitry or a combination of hardwired circuitry and processor-executable program instructions, as also described with respect to system 100 of FIG. 1.

PFT determiner 200 determines PFT values such as FEV1, FVC, FEV1/FVC ratio, and other lung function metrics. The PFT values are determined by PFT determiner 200 based on features that are extracted from audio signal inputs corresponding to a cough event and that are input into a PFT prediction model. As defined herein, "cough" means the sound (characteristically sharp and sudden) generated by a sudden expulsion of air from an individual's lungs. Relatedly, "cough event" is defined as the sounds associated with a single cough or successive coughs occurring within a distinct time interval. The audio signal inputs comprise a series of time-varying electrical signals that are received in real time and/or retrieved from an electronic recordation of audio signals, the audio signals generated by an electrical device in response to a cough event.

The audio signal inputs optionally undergo pre-processing by audio pre-processor 202. Audio pre-processor 202 is capable of performing signal filtering and pre-processing functions such as denoising, smoothing, down sampling, and the like. Audio pre-processor 202, for example, can denoise the audio signal inputs using a high-pass filter with corner frequencies corresponding to a frequency range of human speech and sounds of one or more cough events. The audio signals may be segmented by pre-processor 202 using a sliding window algorithm whose window size corresponds to the duration of a cough event and a Hamming window function. By removing noise and/or spurious content, pre-processor 202 can condition the audio signal inputs for performing signal processing using the various signal processing algorithms described herein.

Sounds captured by a microphone operating in conjunction with PFT determiner 200 can include human speech, ambient noise, and various other sounds, as well as sounds generated by one or more cough events. It is the sounds associated with one or more cough events, however, that are of interest with respect to PFT determiner 200. Accordingly, upon completion of pre-processing by audio pre-processor 202, the microphone-captured audio signals are conveyed to cough detector 204 for filtering out portions of the audio signals that do not relate to a cough event. Cough detector 204 determine which portions of the audio signal correspond to a cough event. Because a cough is typically characterized by relatively higher energy and sudden changes of amplitude in the captured audio signal waveform, cough detector 204 is capable of initially filtering out signal components with below-threshold energy. The threshold can be statistically determined based on corresponding statistical analysis of energy measurements from a sufficiently sized sample of cough events recorded under various conditions within different environments.

The pre-processed and filtered audio signals thus correspond to sounds that potentially are associated with a cough event. Once audio data generated from audio signal input is recognized as corresponding to a potential cough event, the cough detector 204 analyzes the data to distinguish a cough event from other sounds such as normal speech. Cough detector 204 can distinguish a cough event from other sounds (e.g., speech) by classifying the pre-processed and filtered audio signals.

Cough detector 204, in certain embodiments, can classify the pre-processed and filtered audio signals with a classification model constructed using machine learning. Machine learning can be used to generate a classifier, $f: \mathbb{R}^n \to \{1, 2, \ldots, k\}$, which classifies the pre-processed and filtered audio signals. Cough detector 204 generates n-dimensional feature vector representations of the pre-processed and filtered audio signals, and the classifier classifies each n-dimensional feature vector, x, into one of k classes (or categories) based on numeric code $y=f(x)$ determined from the specific values of each of the n elements of x. For example, k=3 for a classifier that classifies filtered audio signals as "cough," "speech," or "other." In one embodiment, the classifier is a logistic regression. In another embodiment, the classifier is a support vector machine (SVM). In yet another embodiment, the classifier is a random forest classifier. In still another embodiment, the classifier is a multi-layer perceptron. Other classifiers generated using machine learning can be used in different embodiments.

The i-th element of each n-dimensional feature vector represents an audio signal feature whose value is determined from the corresponding pre-processed and filtered audio signal that the feature vector represents. Labeled example feature vectors train the classifier using a machine learning rule, and once trained, the classifier classifies audio signals based on feature vectors representative of and corresponding to audio signals generated by a cough event, speech, and other sounds (e.g., ambient noise). The features can include any metric that characterizes an audio signal generated by an electronic device in response to captured sounds such as the user's cough, speech, ambient noise and/or other extraneous sounds. The features include, for example, MFCCs, total signal energy, zero crossing of a signal waveform, and other spectral and waveform features, including statistical measures such as mean, variance, kurtosis, and skewness determined by modeling the audio signals as random processes.

Audio data derived from the portions of the pre-processed or filtered audio signals that cough detector 204, based on a classifier model-determined classification, identifies as a cough event provides the input into cough feature extractor 206. Feature vector generator 208 of cough feature extractor 206 generates from the pre-processed or filtered audio signals identified as corresponding to a cough event, features that are relevant to cough force or other cough characteristic. The features can include cough intensity ("loudness") and/or cough duration (e.g., measured in milliseconds). Other features can include lower-band MFCCs, which represent the short-term power spectrum of sounds generated by a sound (e.g., cough event) based on a linear cosine transform of the log of the power spectrum on a nonlinear mel scale of frequencies and derived as a type of cepstral—that is, an inverse Fourier transform of the logarithm of the estimated signal spectrum—of the audio signal.

The series of audio signals received or retrieved from a recording over time can also be analyzed using statistical signal analysis to determine values of metrics such as the mean, variance, standard deviation, skewness, kurtosis and the like. Accordingly, feature vector generator 208 can generate features that include the mean, variance, kurtosis, and skewness of the audio signal waveform modeled as a random process.

Feature vector generator 208 generates a cough feature vector, v, an n-dimensional vector whose elements are the n cough features extracted from the pre-processed or filtered audio signals. There can be some similarities between the features used by cough detector 204 to detect cough events in a machine learning-based method and those generated by feature vector generator 208. There are many differences, however. The features used by cough feature extractor 206 pertain mainly to cough force and other features related to the cough burst phase or other phase of the audio signal, including, for example, the envelope of a cough waveform, measured area under the graph of a burst phase of the audio signal, the slope of the graph of the burst phase of the audio signal, the wheeziness of the vocal phase of the cough, and the like. Thus, the features used by cough feature extractor 206 are specifically those relevant to cough force and/or other cough characteristics. Cough feature vector, v, is input into regressor 212, which based on the specific values of the n cough features, generates one or more predicted PFT values.

Regressor 212 can implement a regression model generated using machine learning. The machine learning generates a function $g: \mathbb{R}^n \to \mathbb{R}$ that predicts PFT values based on n cough features extracted from the pre-processed and filtered audio signals corresponding to a detected cough event. The regression model implemented by regressor 212 can be trained with data collected from multiple subjects whose coughs provide a statistical sample determining correlations between features of the cough and PFT values typically obtained using pulmonary function testing, such as the FEV1, FVC, FEV1/FVC ratio, and other lung function metrics determined with a spirometer or other pulmonary function testing device.

The parameters of the regression model depend largely on the attributes of the multiple subjects whose coughs are monitored and for whom PFT values are determined for use in training the regression model. Different regression models based on different parameters and/or parameter values, as well as different forms of regression (e.g. linear, non-linear) can be implemented by regressor 212. The particular regression model implemented by regressor 212 can be based on a select sample of subjects chosen based on attributes such as health status, gender, age, and other biodemographic factors. Different regression models, or models based on different sets of model parameters, optionally can be implemented by regressor 212, the different models trained with data from, and corresponding to, different classes of users grouped according to biodemographic and health data (e.g., health status, gender, age). The different parameters correspond to different features extracted from audio signals. Some features are more reliable predictors of PFT values than others depending on user-specific factors. For example, a certain set of MFCCs may be more reliable predictors (inputs to the regression model) for an asthma sufferer, while the skewness of an audio signal as random process is a more reliable predictor for someone afflicted with COPD. An entirely different set of features may provide reliable predictors for a healthy individual.

PFT determiner 200 optionally can store context data 214, the context data providing user-specific, contextual information relating to the user, such as the user's health status, age, gender, and/or other biodemographic characteristics. Data analysis, for example, indicates that skewness is highly correlated to pulmonary function value in COPD patients, which appears not to be the case with asthma patients. Therefore, a user's disease condition can provide context information that is used by feature vector optimizer 210 for selecting particular features or weighting of features according to relevance to specific types of users. Another example of context information is cough wheeziness, which often appears in younger patients. In elderly patients, the wheeziness is often not apparent due to vocal cord changes and the presence of mucus that affects the cough sound. Thus, cough wheeziness is an example feature highly correlated with the age of a user. In general, context data 214 can be used by feature vector optimizer 210 to select one or more specific features from a plurality of features generated by feature vector generator 208, the selection based on the contextual information relating to the user. Context data 214 also can be supplied to regressor 212 for selecting the specific regression model, or particular parameters of the regression model, that is implemented by regressor 212 for determining one or more PFT values. Accordingly, regressor 212 can implement a context-specific regression model based on context data 214 such that the regression model reflects the specific characteristics of the user.

Feature vector optimizer 210, based on context data 214, can select specific features among those generated by feature vector generator 208 for input to regressor 212, which in turn, implements a context-specific regression model that corresponds to the same context data. In certain embodiments particularly beneficial to a user already diagnosed as suffering from a specific pulmonary condition, context data 214 can be used by regressor 212 for implementing a condition-relevant regression model and by feature vector optimizer 210 to select condition-relevant features from among the plurality of features generated by feature vector generator 208. Accordingly, select features (e.g., MFCCs, skewness, kurtosis, voicing parameters) can be cough features used by the condition-relevant regression model, for example, to classify a user's disease state and the severity of the disease.

Figure 3:
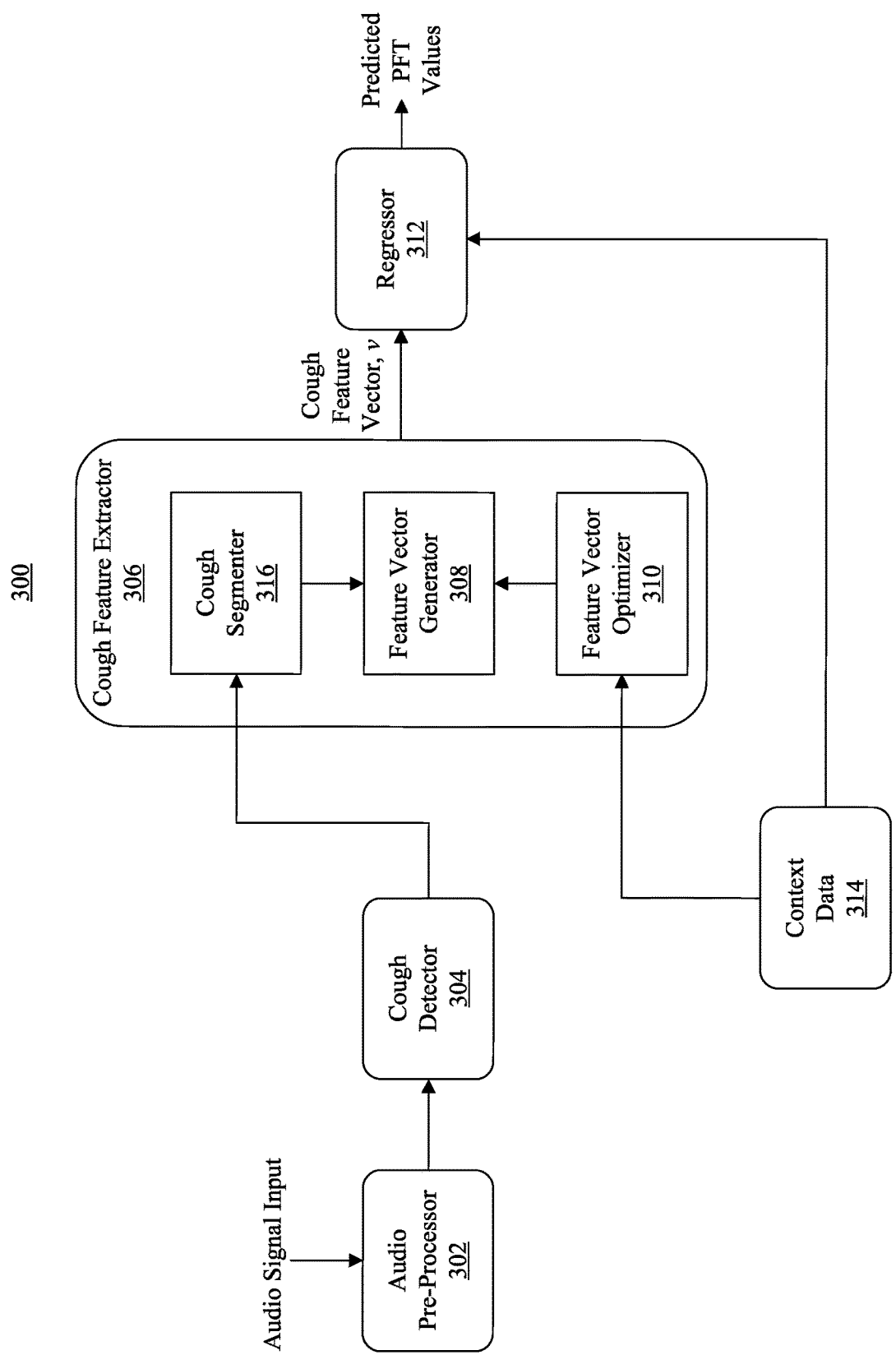
FIG. 3 illustrates an example PFT determiner according to an embodiment.

FIG. 3 illustrates PFT determiner 300 according to another embodiment. PFT determiner 300 illustratively includes audio pre-processor 302, cough detector 304, cough feature extractor 306, feature vector generator 308, feature vector optimizer 310, and regressor 312, which are configured for use with context data 314. Each of the elements performs functions as performed by the comparable elements described with respect to FIG. 2. Additionally, cough feature extractor 306 includes cough segmenter 316, which, like the other elements of PFT determiner 300, can be implemented in processor-executable program instructions, hardwired circuitry, or a combination of circuitry and program instructions.

Operatively, cough segmenter 316 segments portions of audio signal input corresponding to a cough into distinct cough phases. Distinct cough phases can include, for example, a burst phase, followed by a vocal phase, followed by a glottal closure phase. Cough segmenter 316, in certain embodiments, is implemented as a hybrid of machine learning and rule-based procedures. The machine learning aspect of the hybrid procedure is implemented through supervised learning applied to a set of training samples of labeled audio signals corresponding to one or more cough events. The machine learning can be performed using logistic regression, random forest, SVM, or other type of supervised learning. The hybrid procedure implemented by cough segmenter 316 outputs an envelope (a more slowly varying plot of amplitude extremes) of the raw audio signal generated in response to a cough event. The envelope is processed by cough segmenter 316 using multi-level zero-crossing and slope detection procedures.

Figure 4A:
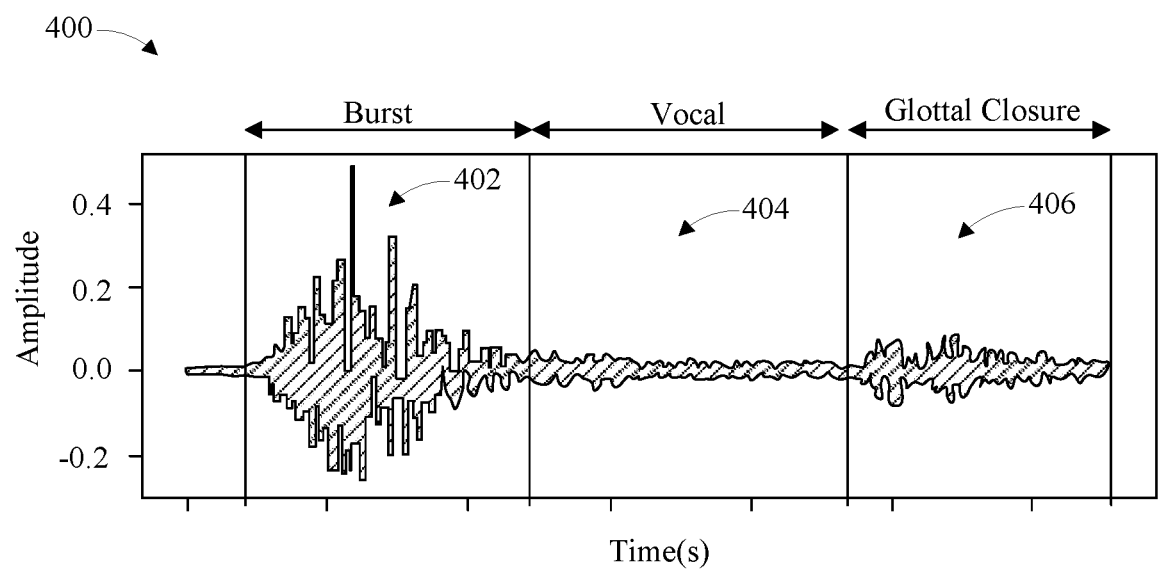
FIGS. 4A and 4B illustrate examples of signal segmentation and resulting cough burst envelopes generated as part of the functions performed by a PFT determiner according an embodiment.
Figure 4B:
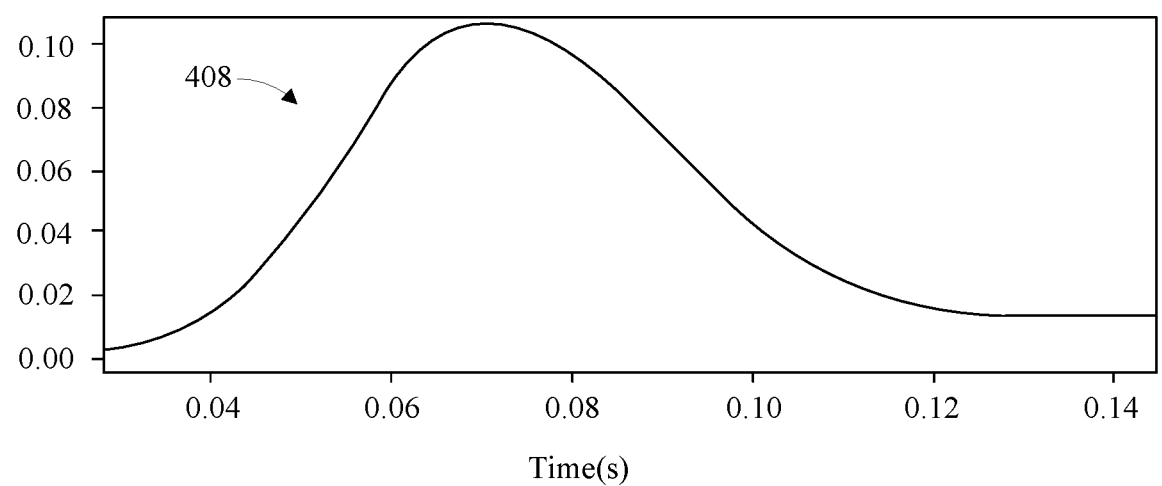

One aspect of the signal processing performed by cough segmenter 316 is extraction of the edges of the burst phase a cough. The burst phase of a cough closely corresponds to the forced exhalation phase detected by a spirometer when testing lung—s using spirometry. FIG. 4A illustrates audio signal 400, which cough segmenter 316 segments into burst phase 402, vocal phase 404, and glottal closure phase 406. FIG. 4B illustrates corresponding envelope 408 of burst phase 402. Cough segmenter 316, by identifying distinct phases of a cough, enables feature vector generator 308 to extract specific cough features that correspond to different phases of the cough, features which can be used to refine the regression model and PFT predictions generated using regression. Feature vector generator 308 can effectively reject the non-burst portions of an audio signal 400 and generate a feature vector based only on specific cough features that correspond to burst phase 402. One aspect of focusing on burst phase 402 and rejecting non-burst portions of the audio signal is that the PFT value(s) determined by PFT determiner 300 based on burst phase 402 correspond closely to the lung function metrics generated by a spirometer due to the similarity between burst phase a cough and lung exhalation relied on with spirometry testing.

An episodic cough event is characterized by a sequence of coughs. Very often with an episodic cough event, the coughs subsequent to an initial cough are less indicative of the forced exhalation that provides a reliable PFT value, whether obtained using a spirometer or other device. This is due to the likely depletion of air in a cougher's lungs after the initial cough. Various other factors and/or other circumstances may make one cough more reliable than others that are part of an episodic cough event when estimating or predicting a PFT value.

Figure 5:
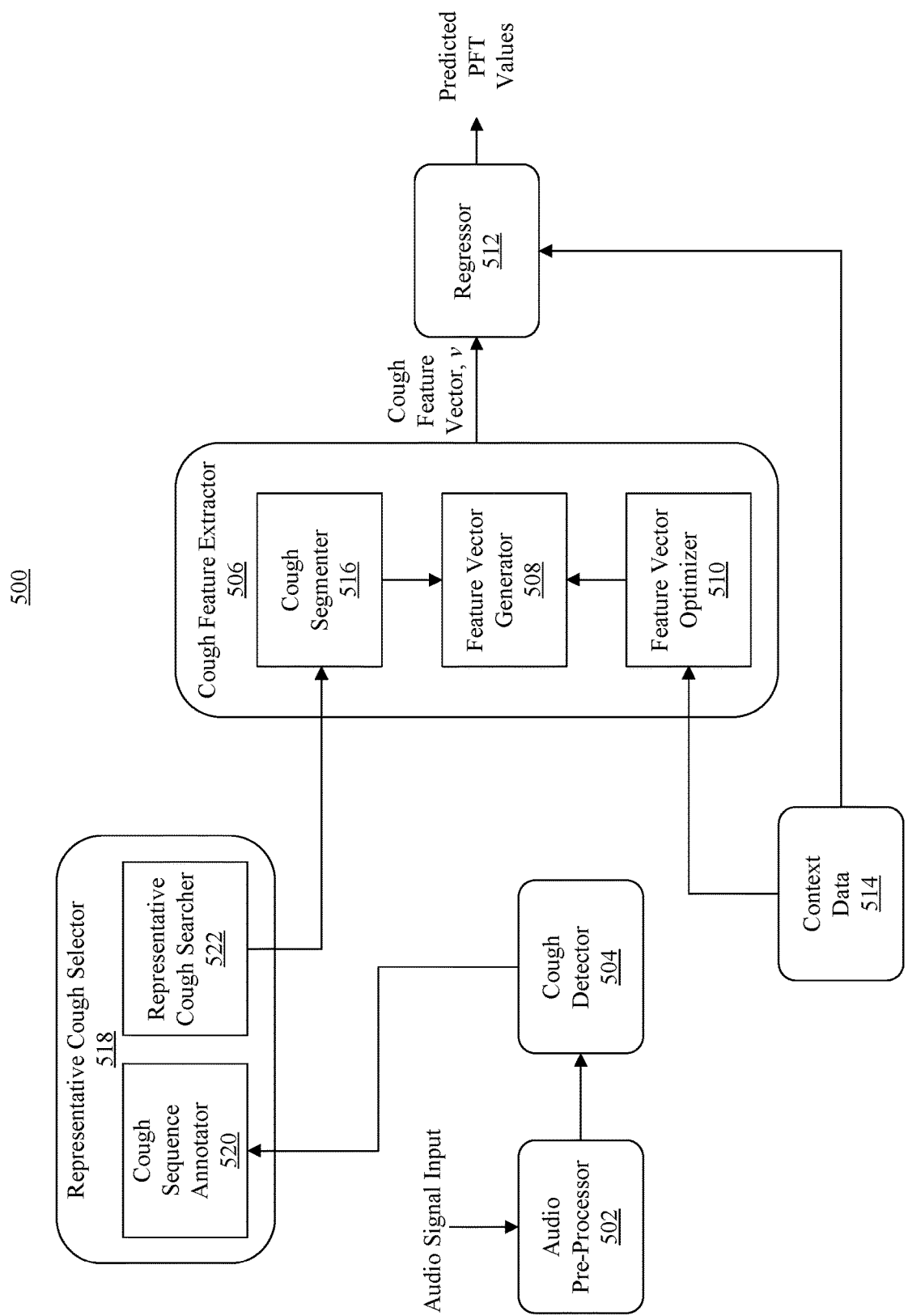
FIG. 5 illustrates an example PFT determiner according to another embodiment.

FIG. 5 illustrates PFT determiner 500, which according to still another embodiment, is adapted to select a specific cough from among a series of coughs detected during a cough event. PFT determiner 500 illustratively includes components comparable to those already described with respect to FIGS. 2 and 3. These include audio pre-processor 502, cough detector 504, cough feature extractor 506, feature vector generator 508, feature vector optimizer 510, and regressor 512, adapted for use with context data 514, as well as cough segmenter 516. PFT determiner 500 additionally includes representative cough selector 518, which is operatively coupled to cough feature extractor 506. Representative cough selector 518 implements cough sequence annotator 520 and representative cough searcher 522. Cough sequence annotator 520 marks or labels each cough of a sequence of coughs detected by cough detector 504 that may be within a cough event. Representative cough searcher 522 can assess the features of each of multiple coughs annotated and can thus identify the most representative cough. Because coughs subsequent to an initial cough are less indicative of the forced exhalation that provides a reliable PFT value, the first cough is most likely the most representative. The cough selected by representative cough selector 518 is input to feature vector extractor 506. Feature vector generator 508 generates features relevant to cough force or other cough characteristic, and feature vector optimizer 510 selects among the generated features based on context data 514. Cough feature vector, v, is input to regressor 512, which generates one or more predicted PFT values based on the selected features, as also described with respect to FIGS. 2 and 3.

More generally, cough sequence annotator 520 annotates each cough within a sequence of coughs, and representative cough searcher 522 selects one of those in the sequence and provides the corresponding portion of audio to cough feature extractor 506. In one aspect, representative cough searcher 522 selects the first cough in the sequence if, as described, the first one is likely to be most representative of a user's lung functioning. In other embodiments, however, representative cough searcher 522 bases the selection on one or more other or additional factors, and depending on the one or more other factors, may select a subsequent one in the sequence if one or more factors indicate that the subsequent cough is more likely representative of the user's lung functioning. Such factors can include, for example, cough amplitude (cough force) or duration, reflecting the fact that a longer, more violent cough is more relevant for PFT estimation. Accordingly, although cough amplitude and duration are often greatest with the first cough in a sequence of coughs, a longer and/or more forceful cough occurring later in a sequence can be the most relevant for PFT estimation in some situations.

Figure 6:
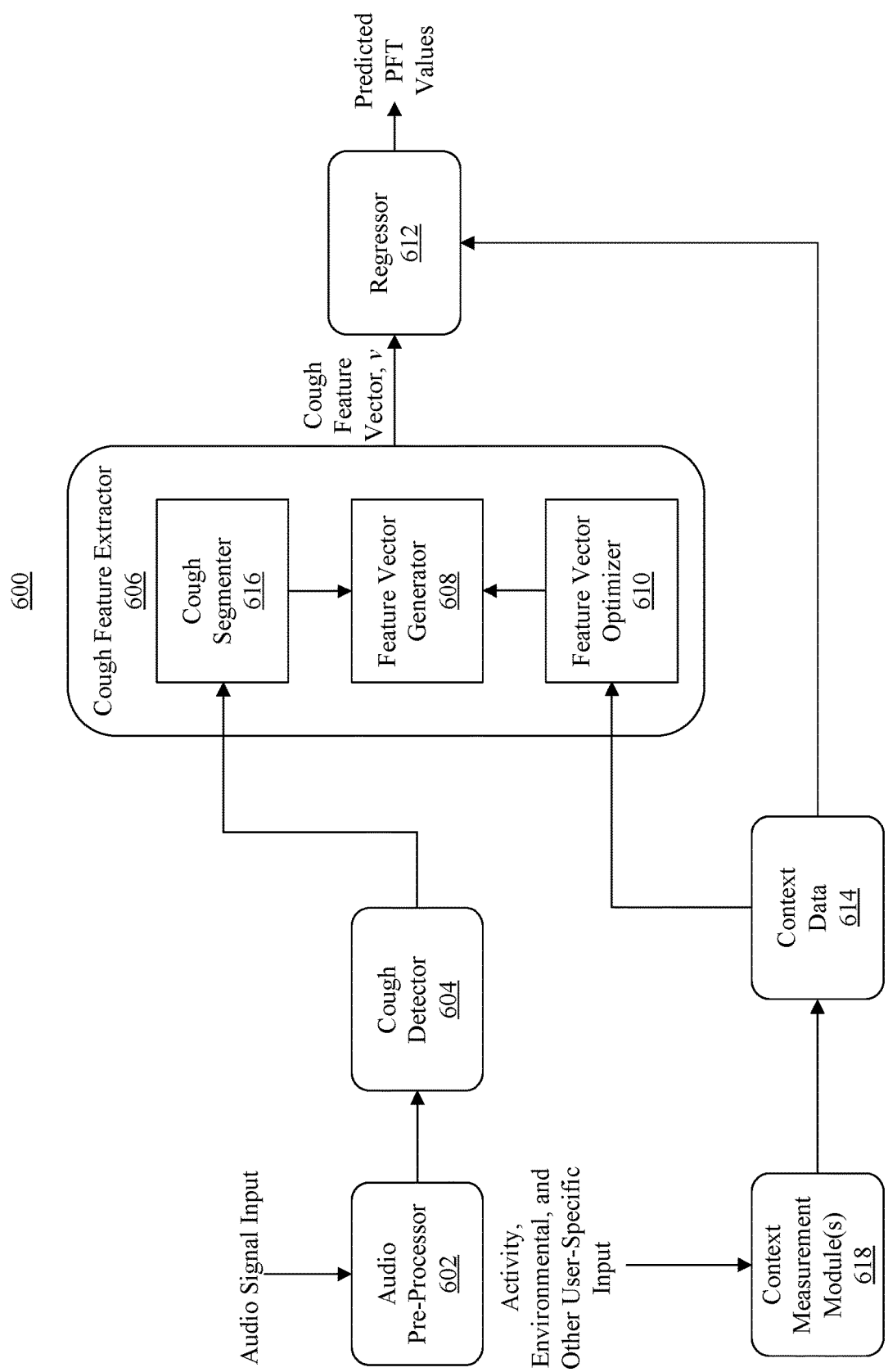
FIG. 6 illustrates an example PFT determiner according to still another embodiment.

FIG. 6 illustrates PFT determiner 600 according to yet another embodiment. PFT determiner 600 includes audio pre-processor 602, cough detector 604, cough feature extractor 606, feature vector generator 608, feature vector optimizer 610, regressor 612, adapted for use with context data 614, and cough segmenter 616, which function as do the comparable components described with respect to FIGS. 2, 3, and 5. PFT determiner 600, however, supplements general biodemographic data 614 with context data determined from sensor data. The sensor data can be generated by a system such as system 100 that include one or more sensors. As illustrated in FIG. 1, the sensors can include, for example, motion sensor, proximity sensor, location sensor, magnetometer, accelerometer, altimeter, heart rate sensor, and the like. The sensors can be included in a system such as a smartphone or smartwatch, for example.

PFT determiner 600 illustratively includes one or more context measurement modules 618. Context measurement modules 618 can generate supplemental context data to supplement context data 614. The supplemental context data is based on sensor data generated by various sensors that can detect and record various user activities such as movements like walking, jogging, or engaging in sport activities. Sensors can, for example, monitor the user's breathing to determine breathing patterns, cough frequency, and the like. Sensors can detect periods marked by the user wheezing or experiencing shortness of breath, for example. One or more location sensors can determine the user's geographic location, which can indicate whether and/or the degree to which the user is exposed to specific environmental conditions (e.g., pollution) that can affect the user's lung functioning.

Whereas context data 614 characterizes the user based on general biodemographic factors such as health status, disease stage or severity, gender, and/or age, the supplemental context data generated by context measurement modules 618 is based on sensor data. The sensor data can be used by context measurement modules 618 to generate data indicative of dynamic factors (e.g., user activity, user environment) specific to the user that also affect the user's lung functioning. The sensor-based data, being dynamically determined in real-time or near real-time, can thus be used in lieu of or in conjunction with context data 614, which is based on general biodemographic factors relevant to the user.

The sensor-based data can be input to feature vector optimizer 610, which determines which features generated by feature generator 608 are selected for input to regressor 612. The sensor-based data can also be input directly to regressor 612 to determine the parameters used to generate predicted PFT values based on the selected features. Accordingly, the predicted PFT values reflect not only general biodemographic characteristics (e.g., health, gender, age) of the user, but also additional factors based on sensor data relating, for example, to the user's physical activity and environment which can affect the user's lung functioning.

Figure 7:
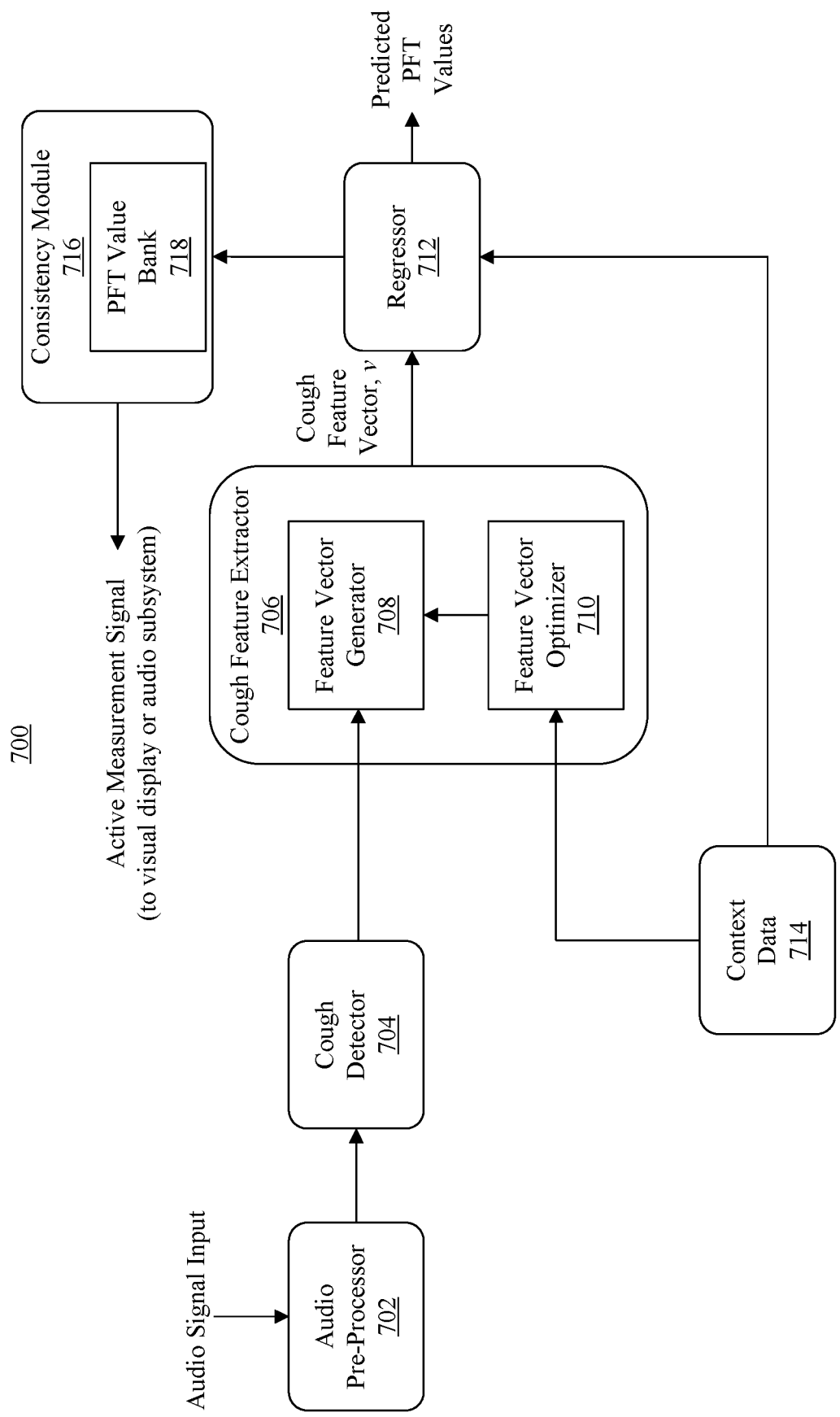
FIG. 7 illustrates an example PFT determiner according to yet another embodiment.

FIG. 7 depicts PFT determiner 700 according to still another embodiment. PFT determiner 700 includes audio pre-processor 702, cough detector 704, cough feature extractor 706, feature vector generator 708, feature vector optimizer 710, regressor 712, adapted for use with context data 714, which function as do the comparable components described with respect to FIG. 2. Additionally, PFT determiner 700 includes consistency determiner 716, which includes PFT value bank 718.

PFT determiner 700 (as well as other embodiments, including PFT determiners 200, 300, 500, and 700) is able to passively monitor a user's lung functioning. The monitoring is passive in the sense that no conscious effort on the part of the user is necessary. A PFT determiner implemented, for example, in a smartphone, smartwatch, or virtual assistant can detect a cough event whenever the smartphone is carried or the smartwatch is worn by the user, or when the virtual assistant is within range to pick up sounds from the user. As described above, the PFT determiners can distinguish sounds associated with one or more cough events from various other sounds. Thus, passive monitoring enables PFT values to be determined with little or no effort of the user.

Consistency determiner 716 of PFT determiner 700 determines whether the quality of the passively sensed cough is sufficient to provide a reliable PFT prediction. A passively sensed cough of quality is one whose volume is consistent and that provides audio signal input whose noise is below a predetermined threshold. PFT value bank 718 provides PFT values against which a PFT value, determined in response to a passively sensed cough event, can be compared by PFT consistency determiner 716. In the event that a PFT value is inconsistent with one or more values stored in PFT bank 718, or if no PFT value can be determined after sensing because of the poor quality of the sensing, PFT consistency determiner 716 responds by issuing an active measurement signal to the user. The active measurement signal can be a text message or recording rendered by a display or audio subsystem (FIG. 1) of a system in which PFT determiner 700 is implemented. The user can be instructed as to how to position the system (e.g., hold an embedded microphone at a specific angle and/or specific distance from the user's mouth) and to voluntarily cough. Active sensing of a cough event, as needed, can provide audio signals inputs of sufficient quality (e.g., consistent volume, reduced noise) to generate a reliable PFT value in the event that obtaining the input through passive sensing is impeded for some reason.

Thus, PFT determiner 700 determines a quality of one or more passive lung function parameter measurements for generating a reliable PFT value. Based on the quality, PFT determiner 700 can determine a manner (e.g., positioning a system) and/or a time for an active lung function parameter measurement. PFT determiner 700, via a display or an audio subsystem, can request the user to perform the active lung function parameter measurement in the specified manner and/or at a specified time.

Figure 8:
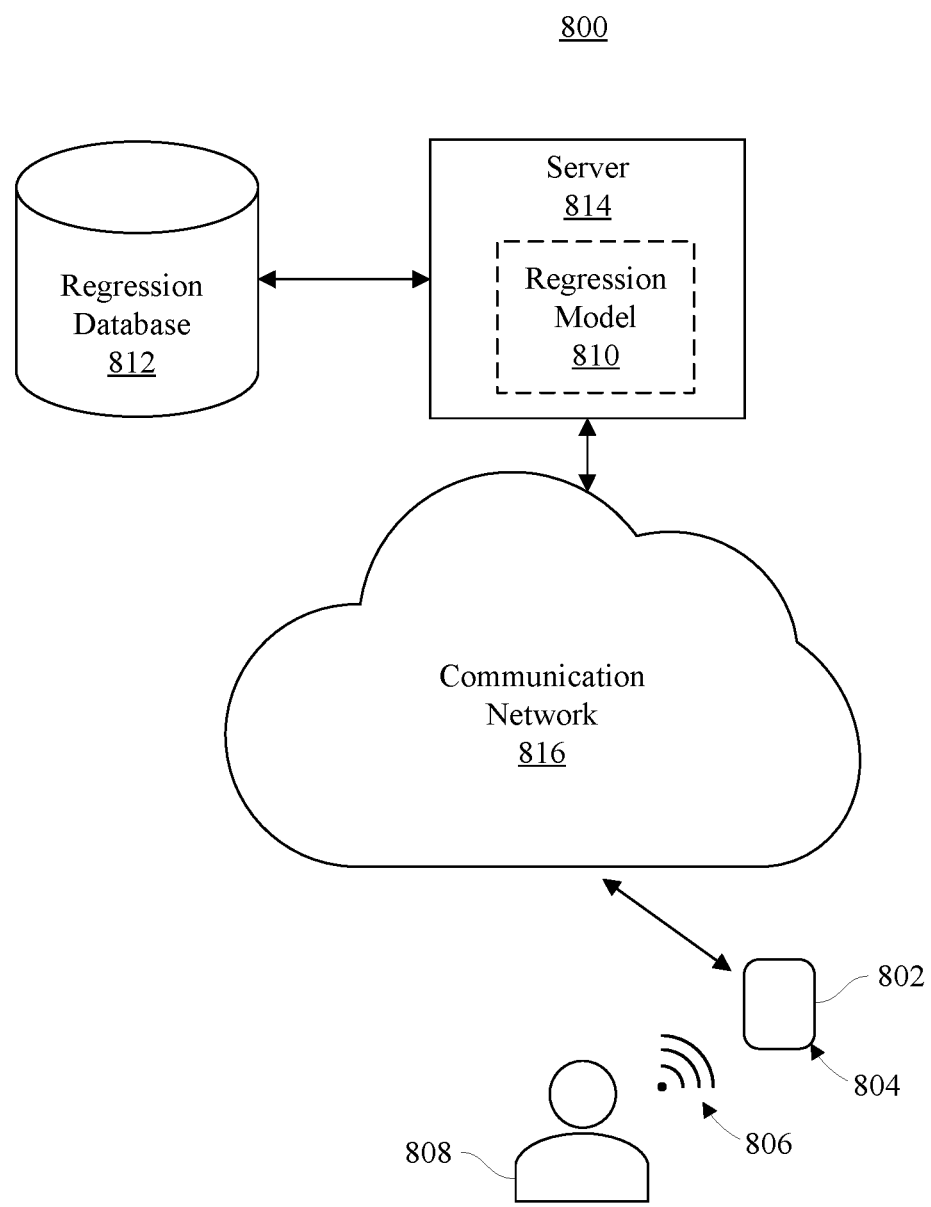
FIG. 8 illustrates an example networking environment of a PFT determiner according to an embodiment.

FIG. 8 illustrates an example networking environment 800 in which system 802, in one or more embodiments, performs various operations for determining lung function metrics. System 802 can be, for example, a smartphone, smartwatch, virtual assistant or other system as described with respect to FIG. 1. System 802 can include a memory, one or more processors, and an audio subsystem. Using the memory, one or more processors, and audio subsystem, system 802 can implement PFT determiner 804 having the capabilities described herein for determining PFT values based on audio signal input 806 generated in response to sounds of one or more cough events of user 808.

PFT determiner 804 can determine PFT values such as FEV1, FVC, FEV1/FVC ratio, and/or other lung function metrics. As described above, the PFT values can be determined based on input comprising features generated and selected by a cough feature extractor. The features are relevant to cough force and/or other cough characteristics and are extracted from audio signal input received in real time and/or retrieved from a recording by system 804 as also described above. The PFT values can be predicted by regression model 810 based on the features generated and selected by the cough force extractor of PFT determiner 804.

Figure 9:
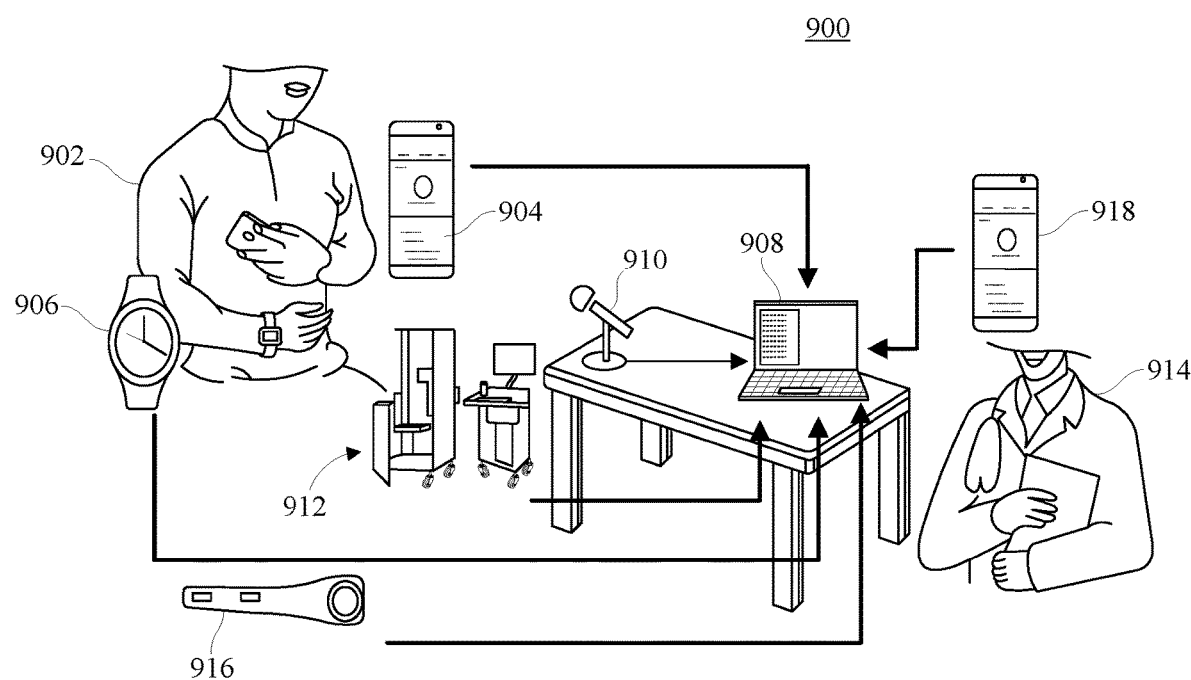
FIG. 9 illustrates an example clinical environment for generating a PFT determiner regression model according to an embodiment.

Regression model 810 can be constructed using machine learning applied to a set of training examples collected from multiple individuals. Referring additionally to FIG. 9, a representative clinical environment for collecting training examples is depicted. As depicted, a cough event of individual subject 902 generates corresponding audio signals, which are sensed using smartphone 904 and/or smartwatch 906 and conveyed to data processing system 908. Optionally, the audio signals can be detected directly by microphone 910 for calibration of the smartphone 904 and/or smartwatch 906 as needed. Spirometer 912 can determine lung function metrics for subject 902 under the supervision of physician 914. Optionally, additional data relating to subject 902 can be collected using, for example, a heart rate monitor (e.g., chestband 916) and/or another sensor. A separate system (e.g., smartphone 918) can time the phases of the cough event, label the phases, and annotate the data generated in response to the cough event. The data provides the training examples to which machine learning is applied for training a regression model. As constructed based on machine learning, the regression model correlates cough features, which are extracted from the audio signals and that relate to cough characteristics (e.g., cough force), with the lung function metrics determined using spirometer 912.

Different regression models incorporating different parameters can be developed based on distinct groups of subjects classified according to biodemographic factors (e.g., health, gender, age), as described above. Referring still to FIG. 8, the different regression models can be electronically stored in regression database 812 communicatively coupled to networked server 814. System 802 can access networked server 814 via communications network 816. For example, system 802 can be a smartphone that accesses the Internet via a cellular network connection. System 802 can store context data relevant to user 808. The context data can indicate that regression model 810 aptly corresponds to specific biodemographic characteristics of user 808. Cough feature extractor of PFT 804 generates and selects cough features based on audio signal input 806. Regression model 810 determines PFT values based on the cough features.

In some embodiments, regression model 810 can be downloaded to a memory of system 802. Regression model 810 (e.g., one of multiple regression models electronically stored in database 812), once selected based on the context data, can be conveyed from networked server 814 to system 802 via communications network 816 for downloading. In other embodiments, the features generated and selected by cough feature extractor executing on system 802 can be conveyed to networked server 814 via communications network 816. Regression model 810 can execute on networked server 814 and determine one or more PFT values. Once determined, the one or more PFT values can be conveyed from networked server 814 to system 802 via communications network 816.

In still another embodiment, PFT data can be collected remotely from multiple voluntary subjects, each subject using a system that is carried (e.g., smartphone), worn (e.g., smartwatch) or stationary (e.g., virtual assistant) for passively monitoring subjects' cough events over time with a PFT determiner implemented in the system. The PFT determiner in each system can incorporate a PFT consistency determiner that initiates active monitoring whenever passive monitoring of a particular cough event yields an invalid or inconsistent estimate of a lung function metric. PFT data can be uploaded over a communications network (e.g., the Internet) from the multiple subjects' systems to a central database accessible by clinicians and researchers.

In yet another embodiment, a physician can passively monitor a patient's lung functioning using a system that implements a PFT determiner. The PFT determiner can incorporate a PFT consistency determiner that initiates active monitoring whenever passive monitoring of a cough event yields an invalid or inconsistent estimate of a lung function metric for the patient. The patient's PFT data can be uploaded over a communications network (e.g., the Internet) to a HIPAA-compliant server that includes a patient portal accessible to the patient and a clinician portal accessible to the patient's physician. Based on the PFT values determined by the PFT determiner, the PFT determiner can identify potential problems with respect to a user's lung functions. For example, PFT values taken over time can show a consistent degradation of a patient's pulmonary health, which can indicate an increased likelihood of an exacerbating event such as an asthma attack. Accordingly, based on the PFT values, a warning or notification can be sent to a patient and the patient's physician if PFT values measured over a predetermined time interval indicate a consistent or accelerating decline in the user's lung functioning. Another notification can recommend performing spirometry testing as soon as possible. For example, the notification can be sent to the patient suggesting that the patient immediately perform testing using a home-based spirometer, the test results from which can complement the passive-based PFT estimation and provide a clinician with a more complete picture of the patient's pulmonary condition and indicate whether further intervention or treatment by the clinician is warranted.

For a user already identified as suffering from a specific condition, the PFT determiner can provide additional monitoring over time. The monitoring is automatic in that the PFT determiner can listen to sounds and detect within the sounds one or more cough events. Active involvement of the user is not needed for the monitoring, other than being within sound distance of the PFT determiner. The PFT determiner in response to determining specific values of one or more PFT metrics determined from a detected cough can signal the user and/or the user's healthcare provider of the likelihood of an impending adverse event.

FIG. 10 illustrates an example method 1000 of pulmonary function estimation. Method 1000 can be performed by a system the same or similar to the system described in reference to FIG. 1. The system at block 1002 can detect one or more cough events from a time series of audio signals generated by an electronic device of a user. The system at block 1004 can determine one or more lung function metrics of the user based on the one or more cough events. The one or more lung function metrics can comprise PFT values, such as FEV1, FVC, and FEV1/FEC ratio.

In one or more embodiments, the PFT values and/or other lung function metrics can be predicted by a prediction model. The prediction model can be a machine learning prediction model implemented by a logistic regression, a SVM, a random forest classifier, or a multilayer perceptron. In one or more embodiments, the one or more cough events can comprise a plurality of cough events, and the system can identify an initial cough event from the plurality of cough events. The one or more lung function metrics can be determined based on the initial cough event.

FIG. 11 illustrates an example method 1100 of estimating pulmonary function based on features relevant to cough force or other cough characteristic(s). Method 1100 can be performed by a system the same or similar to the system described in reference to FIG. 1. The system at block 1102 can detect one or more cough events from a time series of audio signals generated by an electronic device of a user. At block 1104, the system can generate a plurality of features relevant to cough characteristics associated with the one or more cough events. In one or more embodiments, the plurality of features can include a cough intensity, a cough duration, one or more MFCCs, and/or a cough waveform statistic such as a mean, variance, skewness, or kurtosis. The system at block 1106 can select one or more features from the plurality of features, the selecting based on contextual information relating to the user. The system at block 1108 can determine one or more lung function metrics based on the one or more features selected from the plurality of features.

In one or more embodiments, the determining of one or more lung function metrics can be performed by the system using a context-based regression model. The context-based regression model can determine the lung function metrics based on the one or more features selected from the plurality of features. The context-based regression model can correspond to context data relevant to the user. Based on context data relevant to the user, the system selects one of a plurality of available regression models for determining the lung function metrics. The context data can be data relevant to the user's health, gender, age and/or other biodemographic factor. The context data can, in one or more embodiments, additionally include supplemental context data based on data obtained from one or more sensors operatively coupled to and/or embedded in the electronic device of the user.

FIG. 12 illustrates an example method 1200 of estimating pulmonary function based on a segmenting of cough events. Method 1200 can be performed by a system the same or similar to the system described in reference to FIG. 1. The system at block 1202 can segment one or more cough events into a plurality of segments, the one or more cough events detected from a time series of audio signals generated by an electronic device of a user. At block 1204, the system can determine a cough burst segment from the plurality of segments. The system at block 1206 can select one or more features from a plurality of features determined from a time series of audio signals. The one or more features can be selected from the plurality of features based on the cough burst segment. At block 1208 the system can determine one or more lung function metrics based on the one or more features selected.

Figure 13:
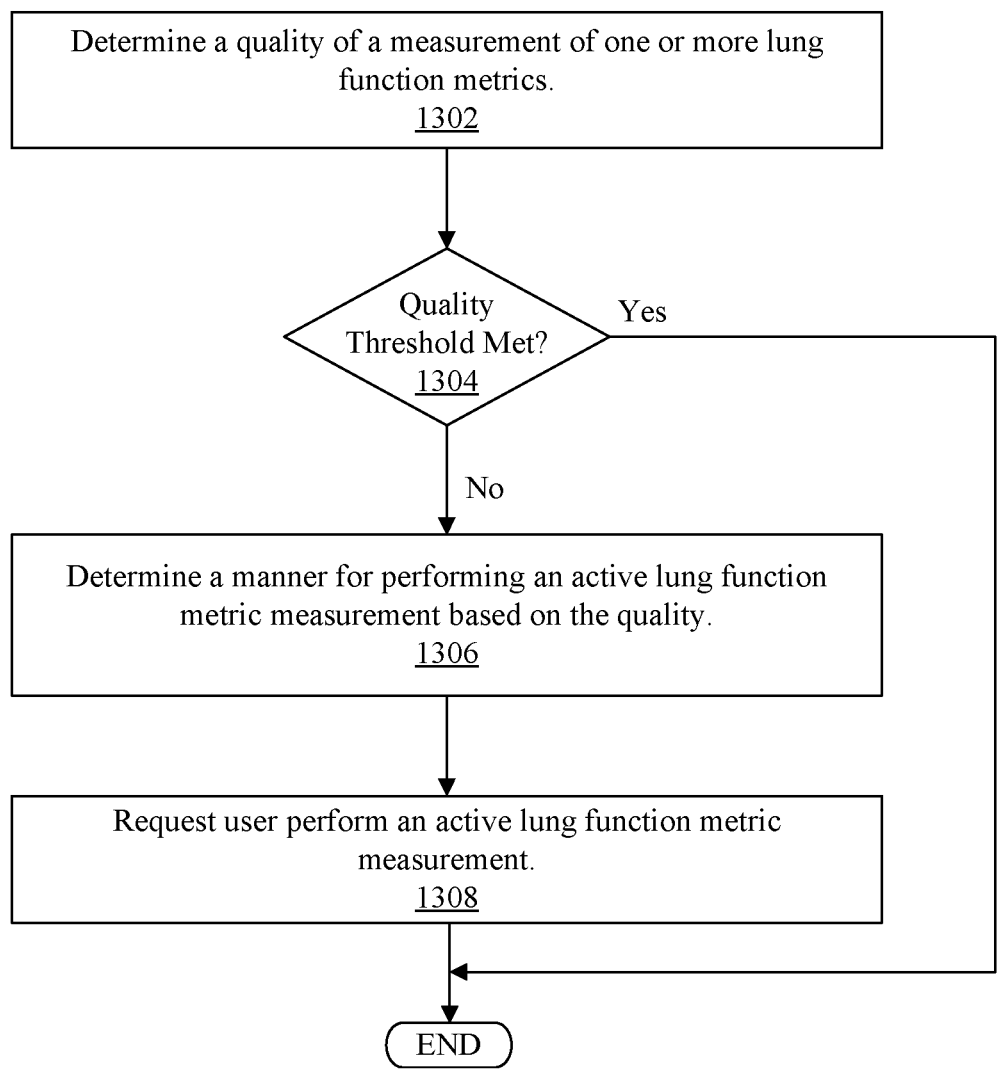
FIG. 13 illustrates an example method of determining a PFT value according to an embodiment.

FIG. 13 illustrates an example method for obtaining estimates of lung function metrics. Method 1300 can be performed by a system the same or similar to the system described in reference to FIG. 1. The system at block 1302 can determine the quality of one or more passive lung function metric measurements. The lung function metric measurements can include PFT values (e.g., FEV1, FVC, FEV1/FEC ratio) determined based on one or more cough events detected from a time series of audio signals generated by an electronic device of a user. At block 1304, the system can determine whether a quality of the measurement meets a predetermined threshold. Optionally, if the quality of the measurement does not meet the predetermined threshold, the system at block 1306 can determine a manner in which an active lung function metric measurement should be performed. The manner can pertain, for example, to the distance and/or angle at which the electronic device should be positioned relative to the user for taking a measurement. The system at block 1308 can request the user perform an active lung function metric measurement. The request can be in response to a determination that the quality of the measurement fails to meet the predetermined threshold. The procedure optionally can be repeated until a lung function metric measurement of acceptable quality is obtained.

The threshold can relate, for example, to noise level and/or volume consistency of the raw audio signal inputs. If the noise level is greater than a predetermined threshold and/or the deviations in volume of the audio signals is greater than the threshold, the quality of the measurement is deemed unacceptable. In one or more other embodiments, the quality of the measurement can be based on a comparison of the lung function metric generated by the system as compared to one or more representative measurements collected from audio signals under idealized or nearly idealized conditions and stored electronically in a database. The predetermined threshold can correspond to the deviation between the system-determined metric and one or more representative measurements. Too large a deviation suggests that the value of the metric determined by the system is likely an outlier or unreliable measurement, thereby necessitating that a new measurement be obtained.

Another quality measurement, for example, can be the number of cough events for which PFT values are determined. If the number of cough events obtained is below a predetermined threshold, the user can be prompted to perform an active lung function metric measurement. Similarly, a quality measurement is below a predetermined threshold if one or more cough events provide a signal strength or cough power that is insufficient to obtain a reliable PFT estimation. Again, the user can be prompted to perform an active lung function metric measurement. In one or more other embodiments, estimated PFT values that exhibit a consistent degradation of lung functioning can indicate a need for performing additional testing to obtain a PFT estimation that can be provided to a clinician alarmed by the degradation as described above. Accordingly, the user can be notified to perform an active lung function metric measurement that is then provided to the clinician.

In still other embodiments, the optionally determined manner for performing an active lung function metric measurement can pertain to a time for taking the measurement. For example, in response to a low quality or possible outlier PFT value, a user can be automatically notified (e.g., via smartphone) to perform an active lung function metric measurement and, if the user is unable to do so at that time, a reminder can be sent (e.g., via smartphone) to the user at a later time.

The terminology used herein is only for the purpose of describing particular embodiments and is not intended to be limiting. Notwithstanding, several definitions that apply throughout this document are now presented.

As defined herein, the singular forms of terms "a," "an," and "the" are intended to include the plural forms as well, unless the context clearly indicates otherwise.

As defined herein, "another" means at least a second or more.

As defined herein, "at least one," "one or more," and "and/or," are open-ended expressions that are both conjunctive and disjunctive in operation unless explicitly stated otherwise. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, "automatically" means without user intervention.

As defined herein, "computer readable storage medium" means a storage medium that contains or stores program code for use by or in connection with an instruction execution system, apparatus, or device. "Computer readable storage medium," as defined herein, is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. Memory elements, as described herein, are examples of a computer readable storage medium. A non-exhaustive list of more specific examples of a computer readable storage medium may include: a portable computer diskette, a hard disk, a random-access memory (RAM), a read-only memory (ROM), an erasable programmable read-only memory (EPROM or Flash memory), a static random-access memory (SRAM), a digital versatile disk (DVD), a memory stick, a floppy disk, or the like.

As defined herein, "includes," "including," "comprises," and/or "comprising," specify the presence of stated features, integers, steps, operations, elements, and/or components, but do not preclude the presence or addition of one or more other features, integers, steps, operations, elements, components, and/or groups thereof.

As defined herein, "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, "one embodiment," "an embodiment," "in one or more embodiments," "in particular embodiments," or similar language mean that a particular feature, structure, or characteristic described in connection with the embodiment is included in at least one embodiment described within this disclosure. Thus, appearances of the aforementioned phrases and/or similar language throughout this disclosure may, but do not necessarily, all refer to the same embodiment.

As defined herein, "output" means storing in physical memory elements, e.g., devices, writing to display or other peripheral output device, sending or transmitting to another system, exporting, or the like.

As defined herein, "processor" means at least one hardware circuit configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application-specific integrated circuitry (ASIC), programmable logic circuitry, and a controller.

As defined herein, "real time" means a level of processing responsiveness that a user or system senses as sufficiently immediate for a particular process or determination to be made, or that enables the processor to keep up with some external process.

As defined herein, "in response to" and "responsive to" mean responding or reacting readily to an action or event. Thus, if a second action is performed "in response to" or "responsive to" a first action, there is a causal relationship between an occurrence of the first action and an occurrence of the second action. The terms "in response to" and "responsive to" indicate the causal relationship.

As defined herein, "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

As defined herein, the terms "user," "individual," "patient," and "subject" mean a human being.

The terms first, second, etc. may be used herein to describe various elements. These elements should not be limited by these terms, as these terms are only used to distinguish one element from another unless stated otherwise or the context clearly indicates otherwise.

Various embodiments of the inventive aspects disclosed herein may be implemented in a system, as a method, and/or in a computer program product at any possible technical detail level of integration. The computer program product may include a computer readable storage medium (or media) having computer readable program instructions thereon for causing a processor to carry out aspects of the embodiments disclosed herein. "Program code" is used interchangeably with "computer readable program instructions" within this disclosure. Computer readable program instructions described herein may be downloaded to respective computing/processing devices from a computer readable storage medium or to an external computer or external storage device via a network, such as the Internet, a LAN, a WAN, and/or a wireless network. The network may include copper transmission cables, optical transmission fibers, wireless transmissions, routers, firewalls, switches, gateway computers, and/or edge devices including edge servers. A network adapter cord or network interface in each computing/processing device receives computer readable program instructions from the network and forwards the computer readable program instructions for storage in a computer readable storage medium with the respective computing/processing device.

Computer readable program instructions for carrying out operations of the inventive arrangements disclosed herein may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language and/or procedural programming languages. The computer readable program instructions may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some embodiments, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products according to embodiments of the inventive arrangements. It will be understood that each block of the flowchart illustrations and/or block diagrams, and combinations of blocks in the flowchart illustrations and/or block diagrams, can be implemented by computer readable program instructions (e.g., program code).

These computer readable program instructions may be provided to a processor of a computer, special-purpose computer or other programmable data processing apparatus to produce a machine, such that the instructions, which execute via the processor of the computer or other programmable data processing apparatus, create means for implementing the functions/acts specified in the flowchart and/or block diagram block or blocks. Operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the inventive arrangements described herein. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments provided herein have been presented for purposes of illustration and are not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art understand the embodiments disclosed herein. Modifications and variations may be apparent to those of ordinary skill in the art without departing from the scope and spirit of the described inventive arrangements. Accordingly, reference should be made to the following claims, rather than the foregoing disclosure, as indicating the scope of such features and implementations.

What is claimed is:

1. A method within and by a computer hardware system including a hardware processor, comprising:
   passively monitoring a time series of audio signals generated by a microphone of the computer hardware system for a cough event by a user;

filtering, by a cough detector within the hardware processor, portions of the audio signals that do not relate to the cough event to generate filtered audio signals;

generating, by a feature vector generator, a cough feature vector corresponding to the filtered audio signals, wherein each element of the cough feature vector corresponds to one or more of a plurality of audio signal features extracted from the filtered audio signals, wherein the plurality of audio signal features includes mean value of mel-frequency cepstral coefficients (MFCCs) and skewness of MFCCs; and generating, by a regressor implemented by the hardware processor, a predicted lung function metric of the user based on the cough feature vector;

wherein the computer hardware system includes a feature vector optimizer configured to select particular ones of the plurality of audio signal features as extracted from the filtered audio signals for inclusion into the cough feature vector based upon one or more biodemographic factors of the user including a health status of the user.

2. The method of claim 1, wherein
the plurality of audio signal features includes cough force.

3. The method of claim 1, wherein
the plurality of audio signal features includes cough wheeziness and the one or more biodemographic factors include age of the user.

4. The method of claim 1, further comprising:
determining, with a geo-positioning sensor, a geographic location of the user;
determining, with the hardware processor, an environmental condition of the geographic location; and
wherein the generating, by the regressor implemented by the hardware processor, the predicted lung function metric of the user is based on the cough feature vector and the environmental condition.

5. The method of claim 1, wherein a context-based regression model is selected from a plurality of context-based regression models to determine the predicted lung function metric based on at least one of the one or more biodemographic factors of the user, and wherein each context-based regression model of the plurality of context-based regression models is based on a distinct group of subjects classified according to the at least one of the one or more biodemographic factors.

6. The method of claim 5, wherein
the regressor is configured to implement a condition-relevant regression model based upon the at least one of the one or more biodemographic factors of the user.

7. The method of claim 1, wherein
the computer hardware system is configured to:
determine a quality of the cough event, at least in part, as an amount of noise in an audio signal provided by the cough event, and
present, via the computer hardware system, an instruction to the user to perform an active lung function metric measurement responsive to the quality of the cough event having the audio signal with the amount of noise above a predetermined threshold.

8. The method of claim 1, wherein
the cough detector includes a cough segmenter configured to extract edges of a burst phase of the cough event and reject non-burst portions of the cough event, and
the cough feature vector is generated only based upon the burst phase of the cough event.

9. The method of claim 1, wherein
the predicted lung function metric is a pulmonary function test value including one or more of FEV1, FVC, or a FEV1/FVC ratio.

10. A computer hardware system, comprising:
a microphone configured to generate a time series of audio signals; and
a hardware processor configured to passively monitor the time series of the audio signals for a cough event by a user, wherein the hardware processor includes
a cough detector configured to filter portions of the audio signals that do not relate to the cough event to generate filtered audio signals;
a feature vector generator configured to generate a cough feature vector corresponding to the filtered audio signals, wherein each element of the cough feature vector corresponds to one or more of a plurality of audio signal features extracted from the filtered audio signals, wherein the plurality of audio signal features includes mean value of mel-frequency cepstral coefficients (MFCCs) and skewness of MFCCs; and
a regressor configured to generate a predicted lung function metric of the user based on the cough feature vector;
wherein the computer hardware system includes a feature vector optimizer configured to select particular ones of the plurality of audio signal features as extracted from the filtered audio signals for inclusion into the cough feature vector based upon one or more biodemographic factors of the user including a health status of the user.

11. The system of claim 10, wherein
the plurality of audio signal features extracted from the filtered audio signals includes cough force.

12. The system of claim 10, wherein
the plurality of audio signal features includes cough wheeziness and the one or more biodemographic factors include age of the user.

13. The system of claim 10, further comprising:
a geo-positioning sensor to determine a geographic location of the user;
an environmental condition determiner configured to determine an environmental condition of the geographic location; and
wherein the regressor is configured to generate the predicted lung function metric of the user based on the cough feature vector and the geographic location.

14. The system of claim 10, wherein a context-based regression model is selected from a plurality of context-based regression models to determine the predicted lung function metric based on at least one of the one or more biodemographic factors of the user, and wherein each context-based regression model of the plurality of context-based regression models is based on a distinct group of subjects classified according to the at least one of the one or more biodemographic factors.

15. The system of claim 14, wherein
the regressor is configured to implement a condition-relevant regression model based upon the at least one of the one or more biodemographic factors of the user.

16. The system of claim 10, wherein
the computer hardware system is configured to:
determine a quality of the cough event, at least in part, as an amount of noise in an audio signal provided by the cough event, and
present, via the computer hardware system, an instruction to the user to perform an active lung function metric measurement responsive to the quality of the cough event having the audio signal with the amount of noise above a predetermined threshold.

17. The system of claim 10, wherein
the cough detector includes a cough segmenter configured to extract edges of a burst phase of the cough event and reject non-burst portions of the cough event, and
the cough feature vector is generated only based upon the burst phase of the cough event.

18. A method within and by a computer hardware system including a hardware processor, comprising:
passively monitoring a time series of audio signals generated by a microphone of the computer hardware system for a cough event by a user;
filtering, by a cough detector within the hardware processor, portions of the audio signals that do not relate to the cough event to generate filtered audio signals;
generating, by a feature vector generator, a cough feature vector corresponding to the filtered audio signals, wherein each element of the cough feature vector corresponds to an audio signal feature extracted from the filtered audio signals; and
generating, by a regressor implemented by the hardware processor, a predicted lung function metric of the user based on the cough feature vector;
wherein the cough detector includes a cough segmenter configured to extract edges of a burst phase of the cough event and reject non-burst portions of the cough event, and the cough feature vector is generated only based upon the burst phase of the cough event.

* * * * *